United States Patent [19]

van Eekelen et al.

[11] Patent Number: 5,733,723
[45] Date of Patent: Mar. 31, 1998

[54] STABLE GENE AMPLIFICATION IN CHROMOSOMAL DNA OF PROKARYOTIC MICROORGANISMS

[75] Inventors: Christiaan A. G. van Eekelen, Bergschenhoek; Johannes C. van der Laan, Amsterdam; Leo J. S. M. Mulleners, Rijen, all of Netherlands

[73] Assignee: Gist-Brocades, Delft, Netherlands

[21] Appl. No.: 295,082

[22] Filed: Aug. 24, 1994

Related U.S. Application Data

[63] Continuation of Ser. No. 893,601, Jun. 3, 1992, abandoned, which is a continuation of Ser. No. 653,977, Feb. 11, 1991, abandoned, which is a continuation of Ser. No. 162,105, Feb. 29, 1988, abandoned.

[30] Foreign Application Priority Data

Feb. 27, 1987 [EP] European Pat. Off. .............. 87200356

[51] Int. Cl.⁶ .............. C12Q 1/68; C12N 15/10; C12N 1/21
[52] U.S. Cl. .............. 435/6; 435/172.3; 435/222; 435/252.31
[58] Field of Search .............. 435/69.1, 172.1, 435/172.3, 252.3, 252.31, 252.2, 320.1, 6, 212, 219, 221, 222

[56] References Cited

U.S. PATENT DOCUMENTS

| Re. 30,602 | 5/1981 | TeNijenhuis | 431/221 |
|---|---|---|---|
| 4,469,791 | 9/1984 | Colson et al. | 435/252.31 |
| 4,959,316 | 9/1990 | Stanislas et al. | 435/252.31 |

FOREIGN PATENT DOCUMENTS

| 0 032 238 | 7/1981 | European Pat. Off. . |
|---|---|---|
| 0 074 553 | 3/1983 | European Pat. Off. . |
| 0 124 374 | 11/1984 | European Pat. Off. . |
| 0 127 328 | 12/1984 | European Pat. Off. . |
| 0 130 756 | 1/1985 | European Pat. Off. . |
| 0 134 048 | 3/1985 | European Pat. Off. . |
| 0 205 371 | 5/1986 | European Pat. Off. . |
| 2 292 042 | 11/1975 | France . |
| WO 86/01825 | 3/1986 | WIPO . |
| WO 87/04461 | 7/1987 | WIPO . |

OTHER PUBLICATIONS

Croft, L.R., "A Compilation of Amino Acid Sequences of Proteins with an Introduction to the Methodology," in: *Handbook of Protein Sequence Analysis*, John Wiley & Sons, pp. 198–199 (1980).
Makino et al., *Agric. Biol. Chem.* (1986) 50:501–504.
Mannarelli & Lacks, *J. Bacteriol.* (1984) 160:867–873.
Niaudet et al., *J. Bacteriol.* (1985) 163:111–120.
Yu et al., *Biol. Abst.: Abst.* 81548 (1986).
Hofemeister et al., Abstract 98:155686a in *Chemical Abstracts* (1983) 98:88.
Kalio et al., Abstract 108:88925n in *Chemical Abstracts* (1988) 108:190.
Williams and Szalay, *Gene* (1983) 24:37–51.
Prozorov et al., *Gene* (1985) 34:39–46.
Yu et al., Abstract 86427, *Biological Abstracts* (1986) 82.
Khasanov et al., *Biological Abstracts* (1986) 81, abstract No. 81548.
Van der Laan et al (1990), "Stable Chromosomal Gene Amplification," in *Genetic Transformation and Expression*, ed. Butler et al (VCH, NY, NY).

*Primary Examiner*—David Guzo
*Attorney, Agent, or Firm*—McDonnell Boehnen Hulbert & Berghoff

[57] ABSTRACT

Transformed prokaryotic hosts are provided comprising two or more copies of a DNA sequence stably maintained in their chromosome, said DNA sequence comprising a gene encoding a polypeptide of interest wherein said copies are separated by endogenous chromosomal DNA sequences. Methods are also provided for producing said transformed host strains. The transformed host strains are capable of increased production of the polypeptide of interest compared to host strains which already produce said polypeptide. Preferred host strains are Bacillus novo species PB92 which produces a high-alkaline proteolytic enzyme and *B. licheniformis* strain T5 which produces a thermostable α-amylase, and mutants and variants of said strains. Preferred polypeptide encoding genes are the protease encoding gene obtainable from Bacillus PB92 and the α-amylase encoding gene obtainable from *B. licheniformis* strain T5.

29 Claims, 23 Drawing Sheets

```
         260                280                300
GAAGCTGTCAGTGAGTTTGTAGAACAAGTAGAGGCAAATGACGAGGTCGCCATTCTCTCT
GluAlaValSerGluPheValGluGlnValGluAlaAsnAspGluValAlaIleLeuSer 320                340                360
                              ─────3─────
GAGGAAGAGGAAGTCGAAATTGAATTGCTTCATGAATTTGAAACGATTCCTGTTTTATCC
GluGluGluGluValGluIleGluLeuLeuHisGluPheGluThrIleProValLeuSer 380                400                420
GTTGAGTTAAGCCCAGAAGATGTGGACGCGCTTGAACTCGATCCAGCGATTTCTTATATT
ValGluLeuSerProGluAspValAspAlaLeuGluLeuAspProAlaIleSerTyrIle 440                460                480
                     ──mat──4──
GAAGAGGATGCAGAAGTAACGACAATGGCGCAATCAGTGCCATGGGGAATTAGCCGTGTG
GluGluAspAlaGluValThrThrMetAlaGlnSerValProTrpGlyIleSerArgVal
```

FIG. 5B

```
                                                                500
CAAGCCCCAGCTGCCCATAACCGTGGATTGACAGGTTCTCGGTGTAAAAGTTGCTGTCCTC
                                                                540
GlnAlaProAlaAlaHisAsnArgGlyLeuThrGlySerGlyValLysValAlaValLeu

560
GATACAGGTATTTCCACTCATCCAGACTTAAATATTCGTGGTGGCGCTAGCTTTGTACCA
                                                                600
AspThrGlyIleSerThrHisProAspLeuAsnIleArgGlyGlyAlaSerPheValPro
          ─────────
              5

620
GGGGAACCATCCACTCAAGATGGGAATGGGCATGTGGCTGGGACGATTGCT
                                                                660
GlyGluProSerThrGlnAspGlyAsnGlyHisValAlaGlyThrIleAla

680
GCTTTAAACAATTCGATTGGCGTTCTTGGCGTAGCACCGAACGCGGAACTATACGCTGTT
                                                                720
AlaLeuAsnAsnSerIleGlyValLeuGlyValAlaProAsnAlaGluLeuTyrAlaVal
      ──────────
          6
```

AAAGTATTAGGGGCGAGCGGTTCAGGTTCGGTCAGCTCGATTGCCCAAGGATTGGAATGG
LysValLeuGlyAlaSerGlySerValSerSerIleAlaGlnGlyLeuGluTrp
                                                   840
         ―――――――――
         7    800

GCAGGGAACAATGGCATGCACGTTGCTAATTTGAGTTTAGGAAGCCCTTCGCCAAGTGCC
AlaGlyAsnAsnGlyMetHisValAlaAsnLeuSerLeuGlySerProSerProSerAla
                         860                                900

ACACTTGAGCAAGCTGTTAATAGCGCGGACTTCTAGAGGCGTTCTTGTTGTAGCGGCATCT
ThrLeuGluGlnAlaValAsnSerAlaThrSerArgGlyValLeuValValAlaAlaSer
                                  ―――――――――
                                  8
                                       920                         960

GGGAATTCAGGTGCAGGCTCAATCAGCTATCCGGCCCGTTATGCGAACGCAATGGCAGTC
GlyAsnSerGlyAlaGlySerIleSerTyrProAlaArgTyrAlaAsnAlaMetAlaVal
```

FIG. 5D

```
              980                   1000                  1020
GGAGCTACTGACCAAAACAACCGGGCCAGCTTTCACAGTATGGCGCAGGGCTTGAC
GlyAlaThrAspGlnAsnAsnArgAlaSerPheSerGlnTyrGlyAlaGlyLeuAsp 1040                 1060                 1080
ATTGTCGCACCAGGTGTAAACGTGCAGAGCACATACCCAGGTTCAACGTATGCCAGCTTA
IleValAlaProGlyValAsnValGlnSerThrTyrProGlySerThrTyrAlaSerLeu
           9                                                  10
                   1100                 1120                 1140
AACGGTACATCGATGGCTACTCCTCATGTTGCAGGTGCAGCAGCCCTTGTTAAACAAAAG
AsnGlyThrSerMetAlaThrProHisValAlaGlyAlaAlaAlaLeuValLysGlnLys 1160                 1180                 1200
AACCCATCTTGGTCCAATGTACAAATCCGCAATCATCTAAAGAATACGGCAACGAGCTTG
AsnProSerTrpSerAsnValGlnIleArgAsnHisLeuLysAsnThrAlaThrSerLeu
```

FIG. 5E

```
                                                1220                          1240                    1260
GGAAGCACGAACTTGTATGGAAGCGGACTTGTCAATGCAGAAGCGGCAACACGCTAATCA
GlySerThrAsnLeuTyrGlySerGlyLeuValAsnAlaGluAlaAlaThrArg 1280                          1300                    1320
ATAAAAACGCTGTGCTTAAAGGGCACAGCGTTTTTTGTGTATGAATCGAAAAGAGAAC
term
```

FIG. 5F

STABLE GENE AMPLIFICATION IN CHROMOSOMAL DNA OF PROKARYOTIC MICROORGANISMS

CROSS REFERENCE TO RELATED APPLICATIONS

This is a continuation of application Ser. No. 07/893,601, filed Jun. 3, 1992, now abandoned, which is a continuation of application Ser. No. 07/653,977, filed Feb. 11, 1991, now abandoned, which is a continuation of application Ser. No. 07/162,105, filed Feb. 29, 1988, now abandoned.

TECHNICAL FIELD

The field relates to prokaryotic cells in which stable gene amplification is obtained by scattered non-tandem integration of at least two copies of a defined DNA sequence into the chromosome of said prokaryotic cell.

BACKGROUND

Bacilli have been widely used for the production of industrially important enzymes such as α-amylase, neutral protease and alkaline or serine proteases (cf. Debabov, "The Industrial Use of Bacilli", in: The Molecular Biology of Bacilli, Acad. Press, New York, 1982). Improvement of production of Bacillus enzymes can be achieved both by classical genetic techniques, such as mutation and subsequent selection, and by modern molecular biological techniques. In the latter case, several ways of obtaining high levels of expression of homologous and heterologous genes in certain prokaryotic and eukaryotic microorganisms by genetic engineering have been well documented.

One of the approaches to achieve high level expression of a gene is to provide the gene with efficient regulatory sequences. Another approach, often used in combination with the first approach, is to increase the copy number of the gene in question. Amplification is primarily achieved by inserting the gene into a multicopy extrachromosomal DNA molecule such as a plasmid. However, a significant drawback of using plasmids as vectors for expressing and amplifying genetic information has been their instability. For large scale use, stability of the amplified gene is a prerequisite for maintaining high level production of the expression product encoded by the amplified gene, as many cell divisions have to take place before sufficient biomass is formed for obtaining substantial product formation.

Instability is encountered in two forms: segregational instability, where loss of the plasmid occurs during cultivation; and structural instability, where a part of the plasmid is deleted. Segregational instability can occur, for example, when a host cell is harboring a vector carrying a gene that is overexpressed. Generally there will be selective pressure towards cells that have lost the capacity to overexpress the gene, since overexpression is an unfavorable property for the transformed host cell. A large amount of metabolic energy is spent on the overexpressed gene product, which negatively influences the cells' competitiveness (growth rate) with host cells not likewise overexpressing.

A method used to counter segregational instability is to select for cells containing multicopy plasmids which carry genes which confer an advantage on the plasmid containing cell, for example, conferring resistance to an antibiotic and then to add the relevant antibiotic to the fermentation broth. However, antibiotics are generally not a useful selection means in large scale commercial production processes due to regulations concerning the approval of the fermentation process or the product itself.

Another method used to minimize plasmid loss due to segregational instability is to insert a gene which is functionally essential for the host cell into the vector (Ferrari et al., *Biotechnology* (1985) 3:1003–1007). However, this method does not ensure structural stability of the vector.

Techniques used to solve the problem of structural plasmid instability have included avoiding expression of the gene during the phase of exponential growth, for example, by using regulatory sequences such as temperature-sensitive regulatory sequences for gene expression. Other methods used have included avoiding the use of autonomously replicating vector molecules and instead using techniques which favor integration of the introduced DNA into the host cell chromosome.

Methods of achieving integration of foreign DNA into the host cell chromosome have included homologous recombination and illegitimate recombination. Two ways of inserting DNA sequences into specific locations on a chromosome by homologous recombination are Campbell-type homologous recombination and double reciprocal recombination, which are shown in FIGS. 1A and 1B, respectively. A third way of introducing DNA sequences into the chromosome, this method using a two-step replacement mechanism, is shown in FIG. 1C. In principle, a Campbell-type recombination is used, but the final result is a chromosomal arrangement that contains no duplicated sequences, and thus no amplifiable unit, in the recombined part of the chromosome. It therefore resembles a double reciprocal recombination.

Apart from using homologous recombination for the integration of foreign DNA into the chromosome it is also possible to integrate DNA by illegitimate recombination. Integrated vector molecules can be selected for under conditions which inhibit autonomous replication of non-integrated vector molecules. Use of illegitimate recombination for integration is depicted in FIG. 1D. The absence of tandem duplications in the obtained chromosomal sequence arrangements make the pathways shown in FIGS. 1B, C and D preferred for stable introduction of DNA sequences into the genome. Chromosomally integrated genes have included both homologous and heterologous genes where the amplification of the chromosomally integrated DNA has been in a tandem array. These chromosomally amplified sequences have been reported to be unstable although stability has been reported in some cases. It is therefore desirable to develop methods whereby DNA integrated into the chromosome is stably maintained.

Relevant Literature

Integration of exogenous DNA by homologous recombination into the chromosome of *Bacillus subtilis* has been described by Duncan et al., *Proc. Natl. Acad. Sci. USA* (1978) 75:3664–3668 and for *Anacystis nidulans* by Williams and Szalay, *Gene* (1983) 24:37–51 and in International Patent Application WO 84/00381. Integration by homologous recombination of a heterologous gene, which cannot be maintained stably when carried on a plasmid vector, into the chromosome of a microorganism is described in EP-A-0127328.

Amplification of chromosomally integrated genes, both homologous and heterologous has been documented. See, for example: Saito et al., *Proceedings of the Fourth International Symposium on Genetics of Industrial Microorganisms*, Kyoto, Japan, 1982, pp. 125130; Young, *J. Gen. Microbiol.* (1984) 130:1613–1621; Janniere et al., *Gene* (1985) 40:47–55; Sargent and Bennett, *J. Bacteriol.* (1985) 161:589–595; Gutterson and Koshland, *Proc. Natl. Acad. Sci. USA* (1983) 80:4894–4898; Hashiguchi et al., Agric. Biol. Chem. (1985) 49:545–550; Wilson and Morgan, *J. Bacteriol.* (1985) 163:445–453; French Patent Application No. 84.06701; and EP-A-0134048. Spontaneous amplification in prokaryotic cells has been reported and can be selected for. See for example the review by Anderson and Roth, *Ann. Rev. Microbiol.* (1977) 31:473–505.

In all cases referred to above, amplification of chromosomally integrated DNA was in a tandem array. This type of chromosomal amplification sequence has been reported to be unstable, although rather good stability was found in some cases, as discussed by Janniere et al., *Gene* (1985) 40:47–55.

Stabilization of naturally occurring amplified prokaryotic genes due to the presence of other essential genes between these amplified sequences has been reported. For example, of the 9 to 10 copies of the ribosomal RNA gene sets occurring in the *B. subtilis* chromosome, two tandemly located sets were separated by a cluster of tRNA genes (Wawrousek and Hansen, *J. Biol. Chem.* (1983) 258:291–298). In other cases, naturally occurring tandemly repeated ribosomal RNA operons were deleted, both in *E. coli* and in *B. subtilis*, with little effect on the phenotypic properties of the organism: Ellwood and Momura, *J. Bacteriol.* (1980) 143:1077–1080 and Loughney et al., *J. Bacteriol.* (1983) 154:529–532, respectively.

Integration of plasmids into the chromosome of *B. subtilis* by illegitimate recombination using the vector pE194 has been described by Hofemeister et al., *Mol. Gen. Genet.* (1983) 189:58–68 and Prorozov et al., *Gene* (1985) 34:39–46.

Several genes for extracellular enzymes of bacilli have been successfully cloned, such as the α-amylase genes of *B. amyloliquefaciens* (Palva et al., *Gene* (1981) 15:43–51), *B. licheniformis* (Ortlepp, *Gene* (1983) 23:267), *B. stearothermophilus* (Mielenz et al., *Proc. Natl. Acad. Sci. USA* (1983) 80:5975–5979; EPA-0057976) and *B. subtilis* (Yang et al., *Nucleic Acids Res.* (1983) 11:237); the levansucrase gene of *B. subtilis* (Gay et al., *J. Bacteriol.* (1983) 153:1424); the neutral protease encoding genes of *B. stearothermophilus* (Fuji et al., *J. Bacteriol.* (1983) 156:831), *B. amyloliquefaciens* (Honjo et al., *J. Biotech.* (1984) 1:165) and of *B. subtilis* (Yang et al., *J. Bacteriol.* (1984) 160:115); the serine or alkaline protease encoding genes of *B. subtilis* (Wong et al., *Proc. Natl. Acad. Sci. USA* (1984) 81:1184), *B. licheniformis* (Jacobs et al., *Nucleic Acids Res.* (1985) 13:8913) and *B. amyloliquefaciens* (Wells et al., *Nucleic Acids Res.* (1983) 11:7911).

Protoplast transformation for several species of gram positive microorganisms has been reported. For *B. subtilis* a protocol for protoplast transformation was described by Chang and Cohen (*Mol. Gen. Genet.* (1979) 168:111–115), which has been widely used. Similar successful protocols have been described for the transformation of *B. megaterium* protoplasts (Vorobjeva et al., *FEMS Microbiol. Letters* (1980) 7:261–263), *B. amyloliquefaciens* protoplasts (Smith et al., *Appl. and Env. Microbiol.* (1986) 51:634), *B. thuringiensis* protoplasts (Fisher et al., *Arch. Microbiol.* (1981) 139:213–217), *B. sphaericus* protoplasts (McDonald, *J. Gen. Microbiol.* (1984) 130:203), and *B. larvae* protoplasts (Bakhiet et al., *Appl. and. Env. Microbiol.* (1985) 49:577); in the same publication unsuccessful results were reported for *B. popillae*. The protocol was successful for *B. polymyxa*, *B. licheniformis*, *B. macerans* and *B. laterosporus*, but not for *B. coagulans*, *B. cereus* and *B. pumilus* even though good protoplast formation was observed (Mann et al., *Current Microbiol.* (1986) 13:131–135).

Other methods of introducing DNA into protoplasts include fusion with DNA containing liposomes (Holubova, *Folia Microbiol.* (1985) 30:97), or protoplast fusion using a readily transformable organism as an intermediate host cell (EPA-0134048).

SUMMARY OF THE INVENTION

Prokaryotic host cells, and methods for their preparation, are provided which comprise at least two copies of a DNA sequence encoding a polypeptide of interest stably integrated into the host cell chromosome. Stable maintenance of the exogenous DNA sequence is obtained by integrating two or more copies of the sequence into the host cell chromosome wherein the copies are separated by endogenous chromosomal DNA sequences.

T is the target sequence, i.e., DNA sequences present on chromosome and plasmid, between which homologous recombination can take place.

S stands for the DNA sequence to be integrated in the chromosome.

M stands for a marker gene sequence used for the selection of recombinant strain.

Figure 2A:
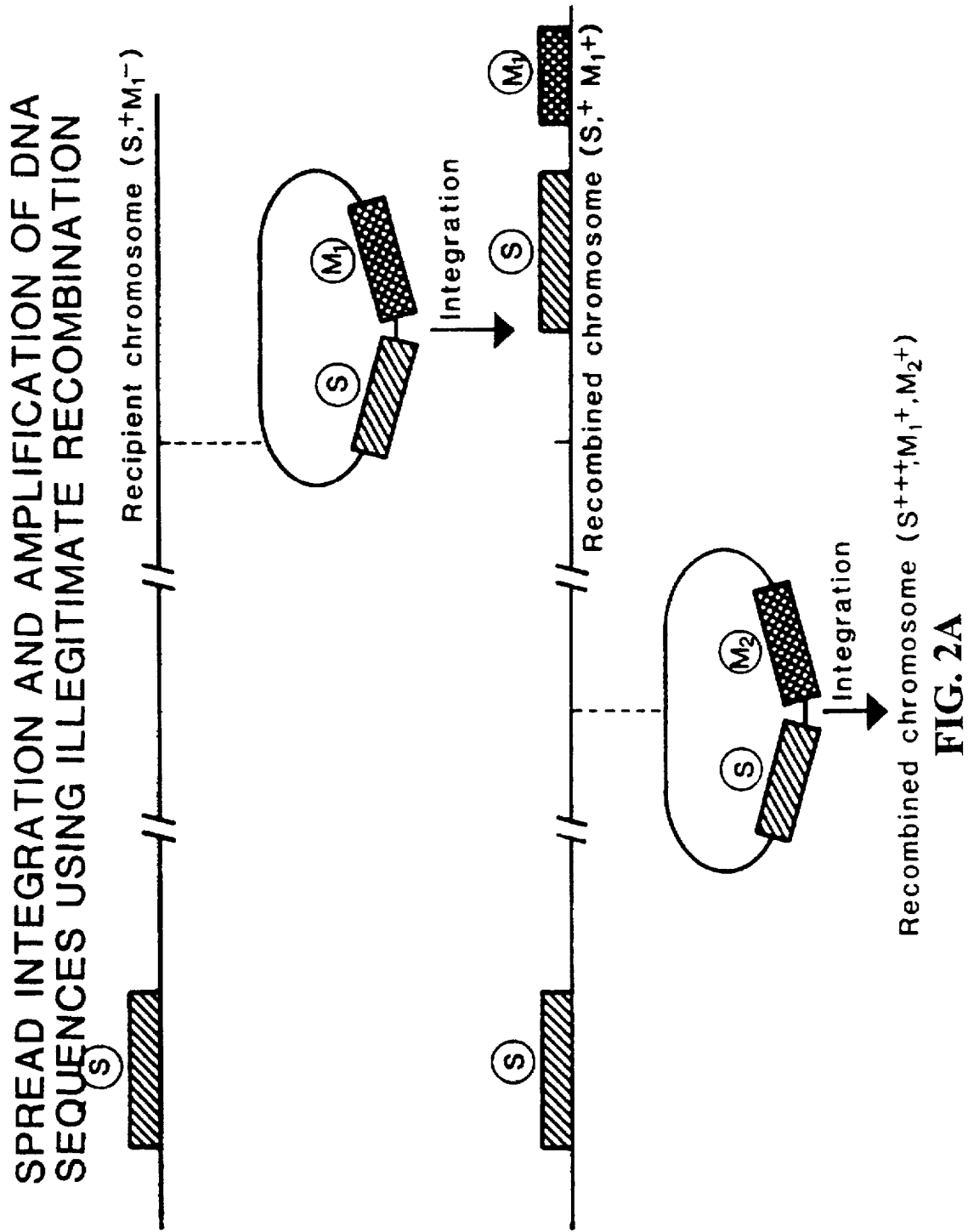
Figure 2B:
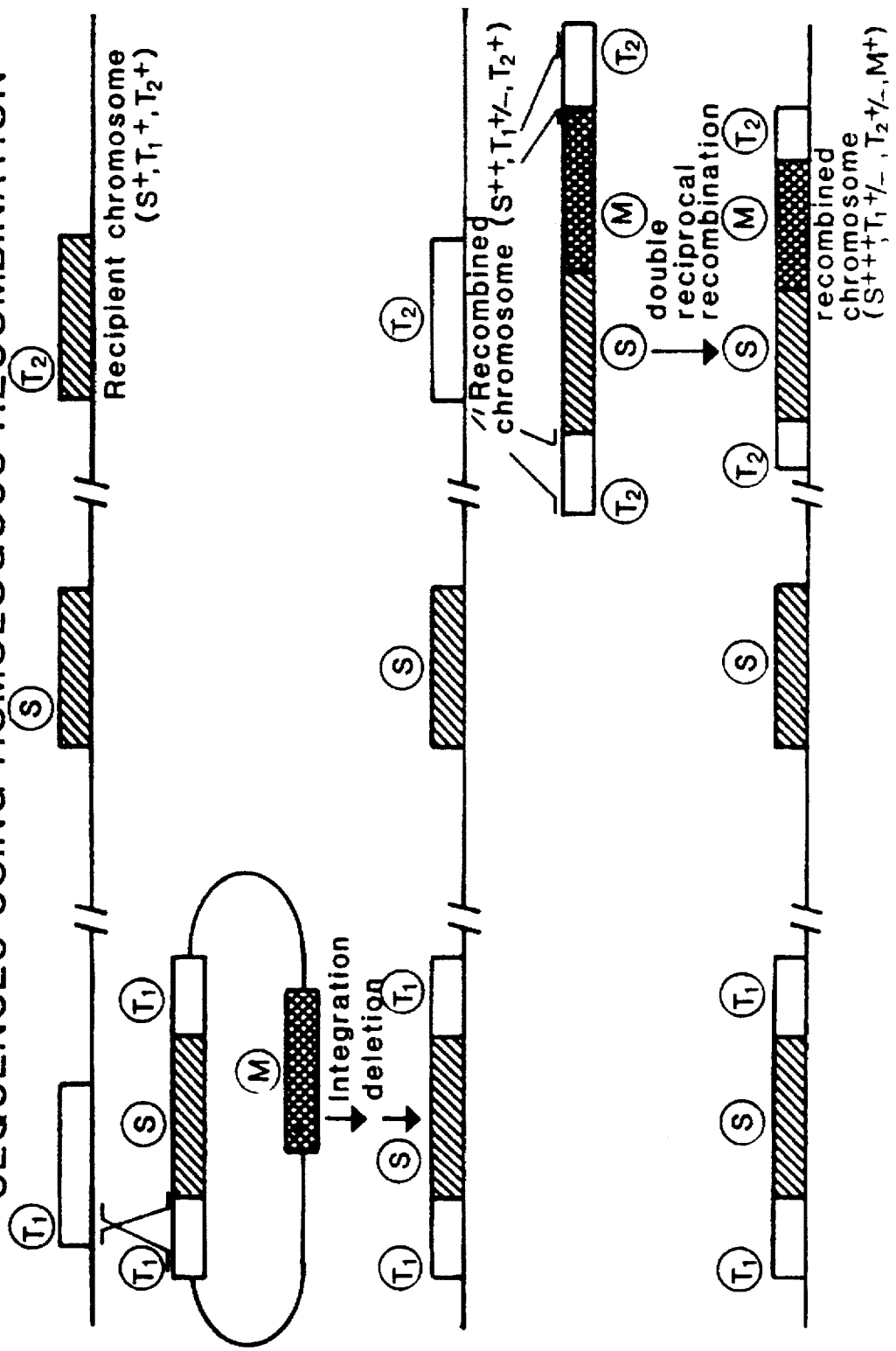

FIGS. 2A and 2B are schematic representations of two ways for obtaining stable gene amplification in a prokaryotic chromosome.

Figure 3:
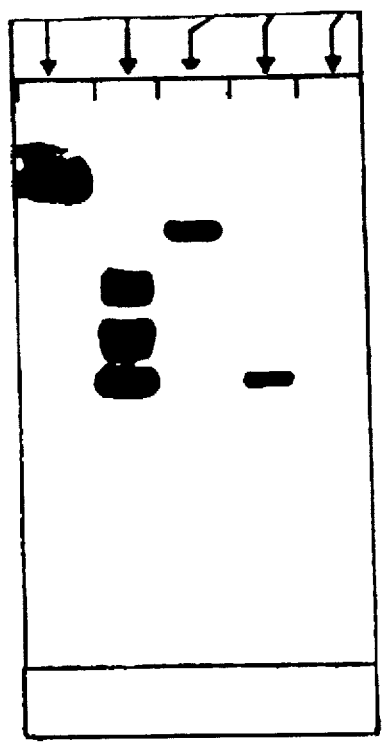

FIG. 3 shows the results of histidine/MOPS gel electrophoresis performed on supernatant from cultures of *B. subtilis* DB104 containing pUB110 and pM58, respectively, compared with several subtilisins:

Lane 1: Carlsberg subtilisin.

Lane 2: Bacillus PB92 protease.

Lane 3: *B. subtilis* subtilisin.

Lane 4: *B. subtilis* DB104 (pM58).

Lane 5: *B. subtilis* DB104 (pUB110).

Figure 4:
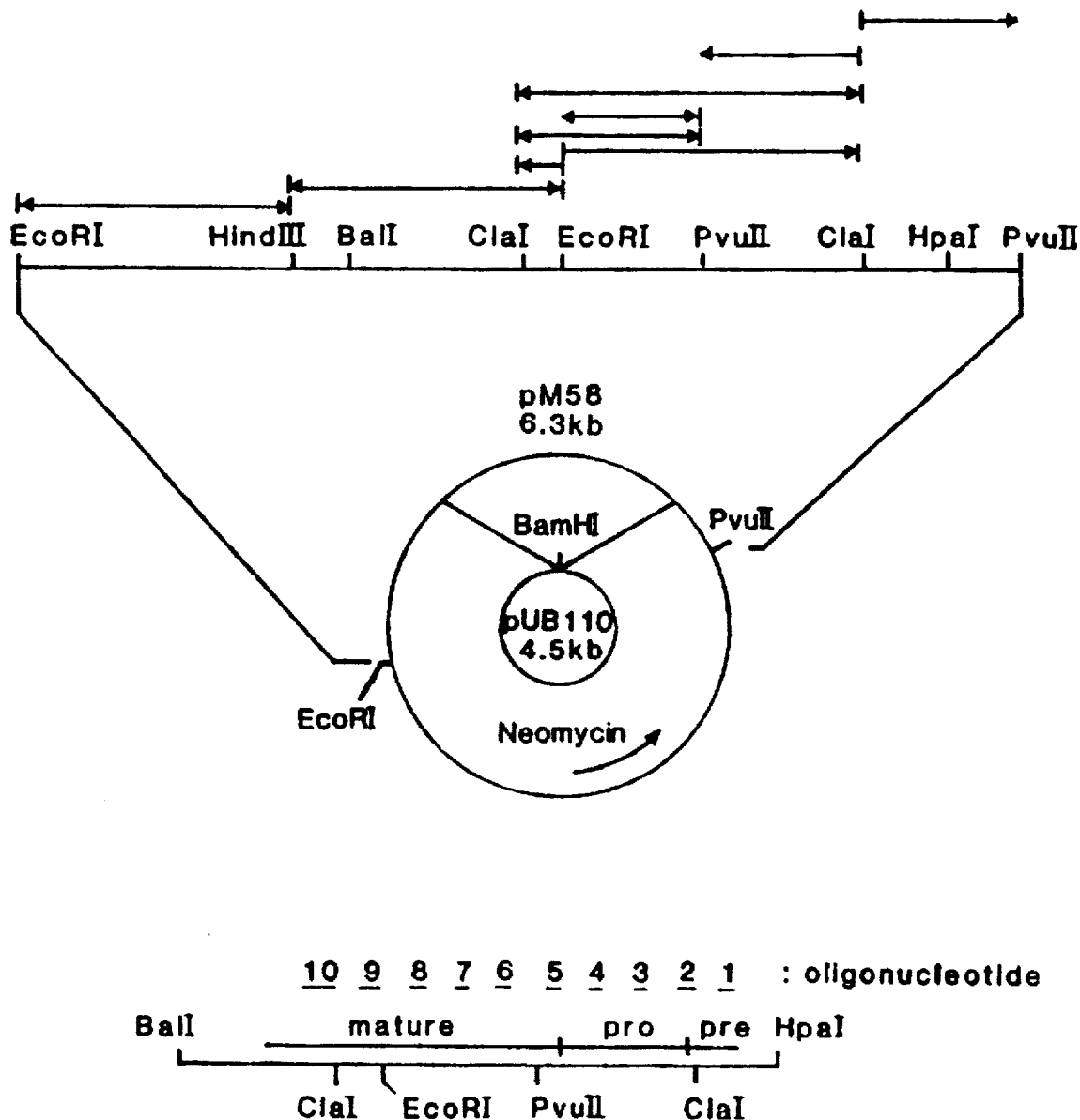

FIG. 4 shows the restriction map of plasmid pM58. Furthermore, the sequencing strategy is shown in the upper part of the figure. The arrowed solid lines represent the fragments cloned in the phage M13 vectors mp10, mp11 and mp18. The lower part of the figure shows the sequencing strategy using ten oligonucleotides located at regular distances on the protease gene.

FIG. 5 shows the nucleotide sequence of the coding strand correlated with the amino acid sequence of Bacillus PB92 serine protease. Promoters ($P_1$, $P_2$), ribosome binding site (rbs) and termination regions (term) of the DNA sequence are also shown. The numbered solid lines represent the location of the ten oligonucleotides used for sequencing.

Figure 6A:
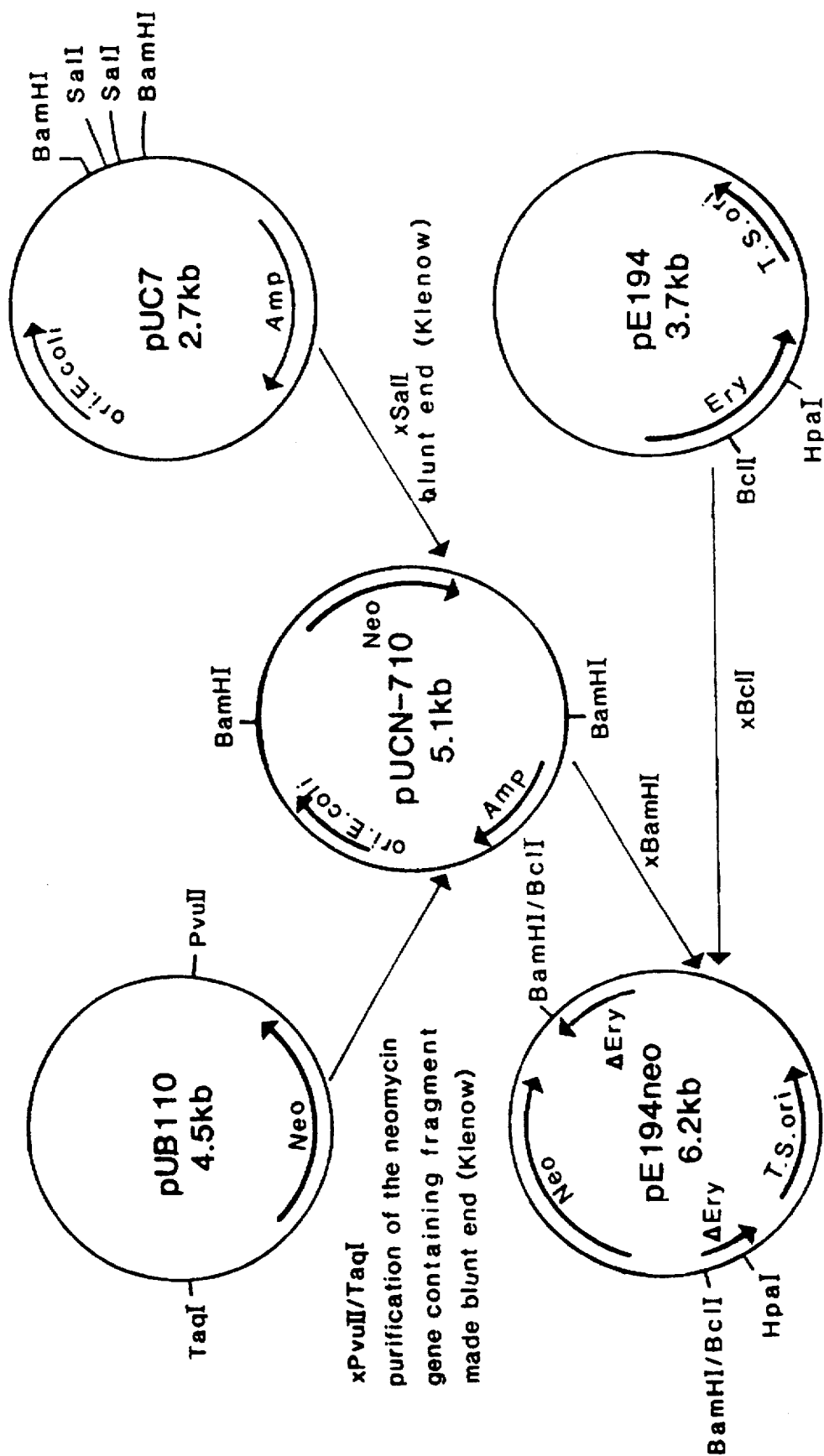

FIG. 6A shows the construction of plasmid pE194-neo.

Figure 6B:
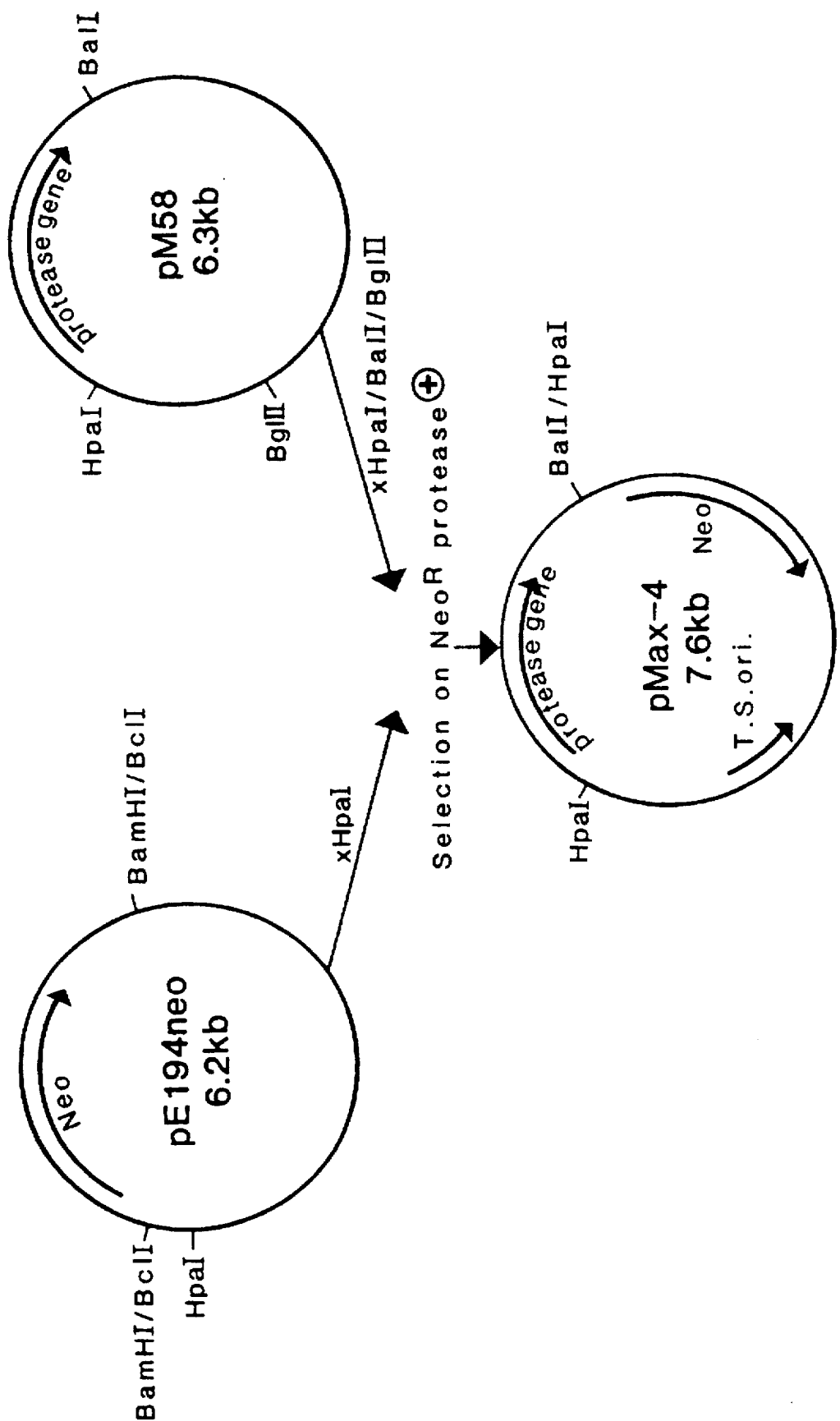

FIG. 6B shows the construction of plasmid pMAX-4.

Figure 7A:
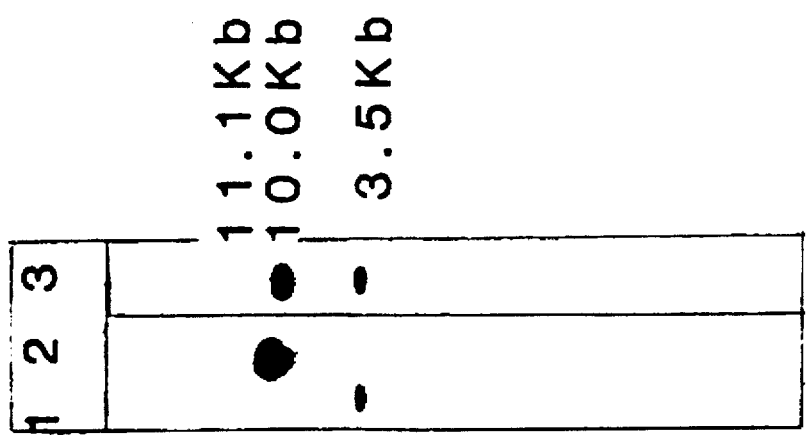

FIG. 7A: Digests prepared with HindIII of chromosomal DNA of the strains PB92, PBT109 and PBT108 were subjected to electrophoresis on a 0.5% agarose gel, transferred to nitrocellulose as described by Southern and hybridized with $^{32}$P labeled nick-translated pM58 DNA. The figure shows an autoradiograph.

Figure 7B:
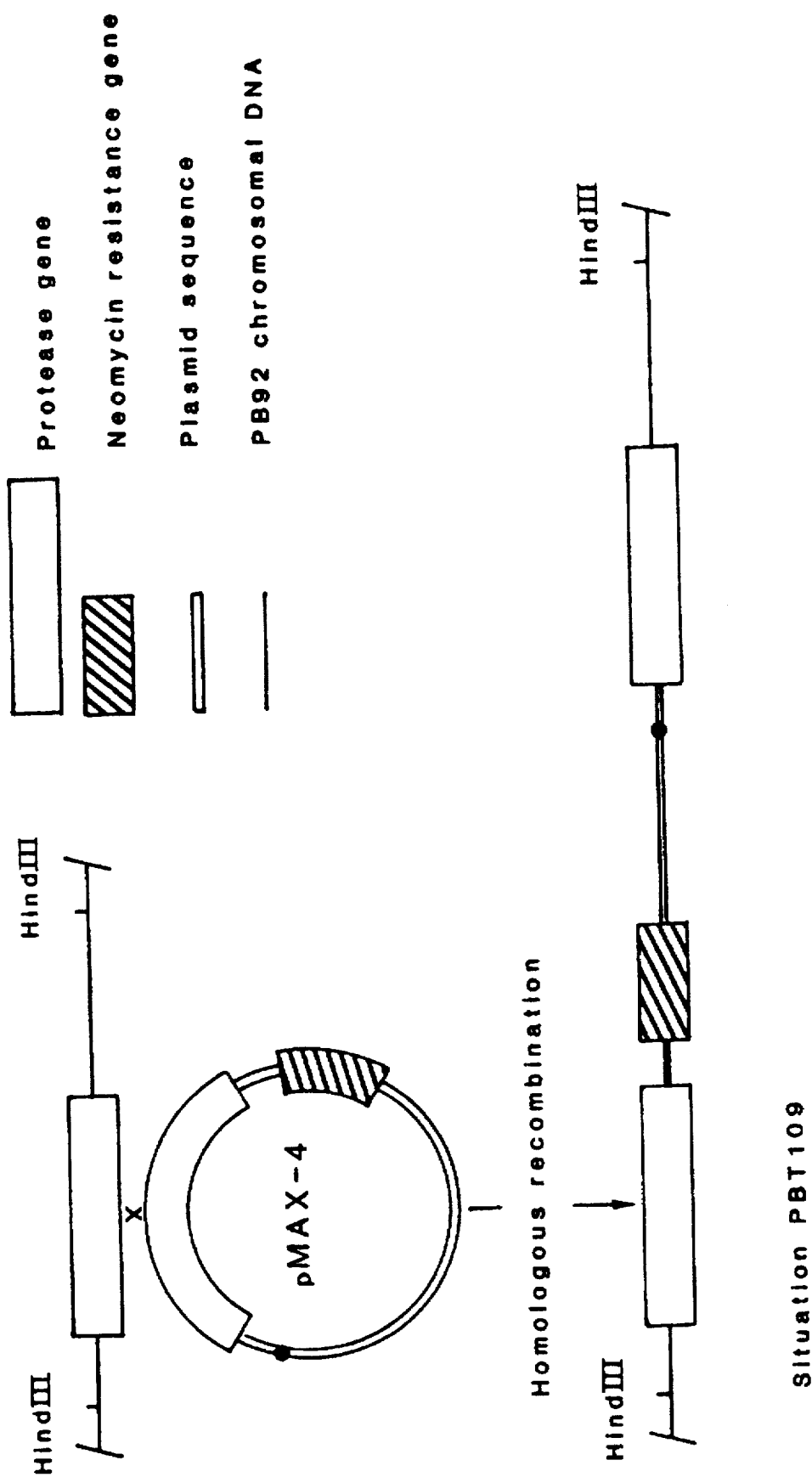
Figure 7C:
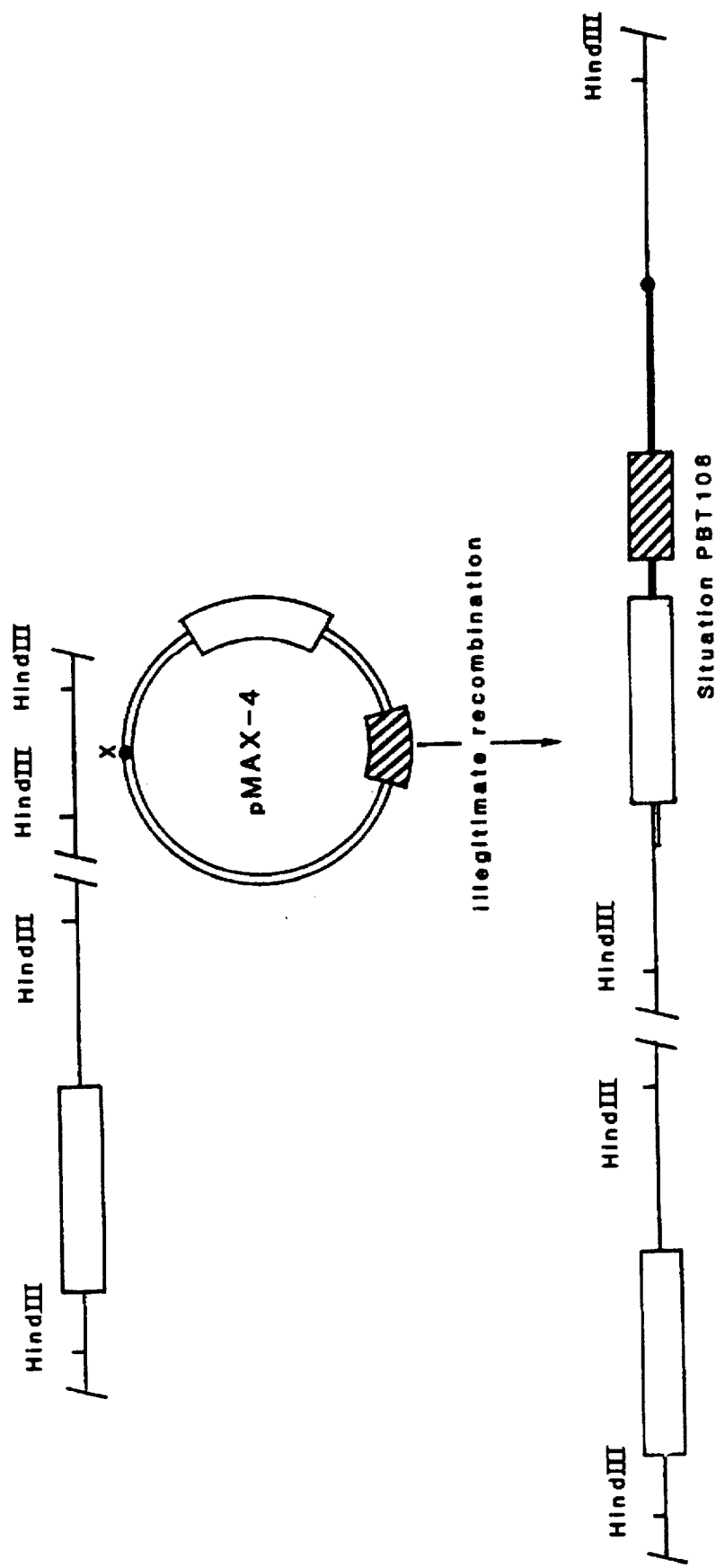

FIGS. 7B and 7C illustrate the integration events occurring in case of homologous (B) recombination and illegitimate (C) recombination between pMAX-4 and the Bacillus PB92 chromosome.

Figure 8:
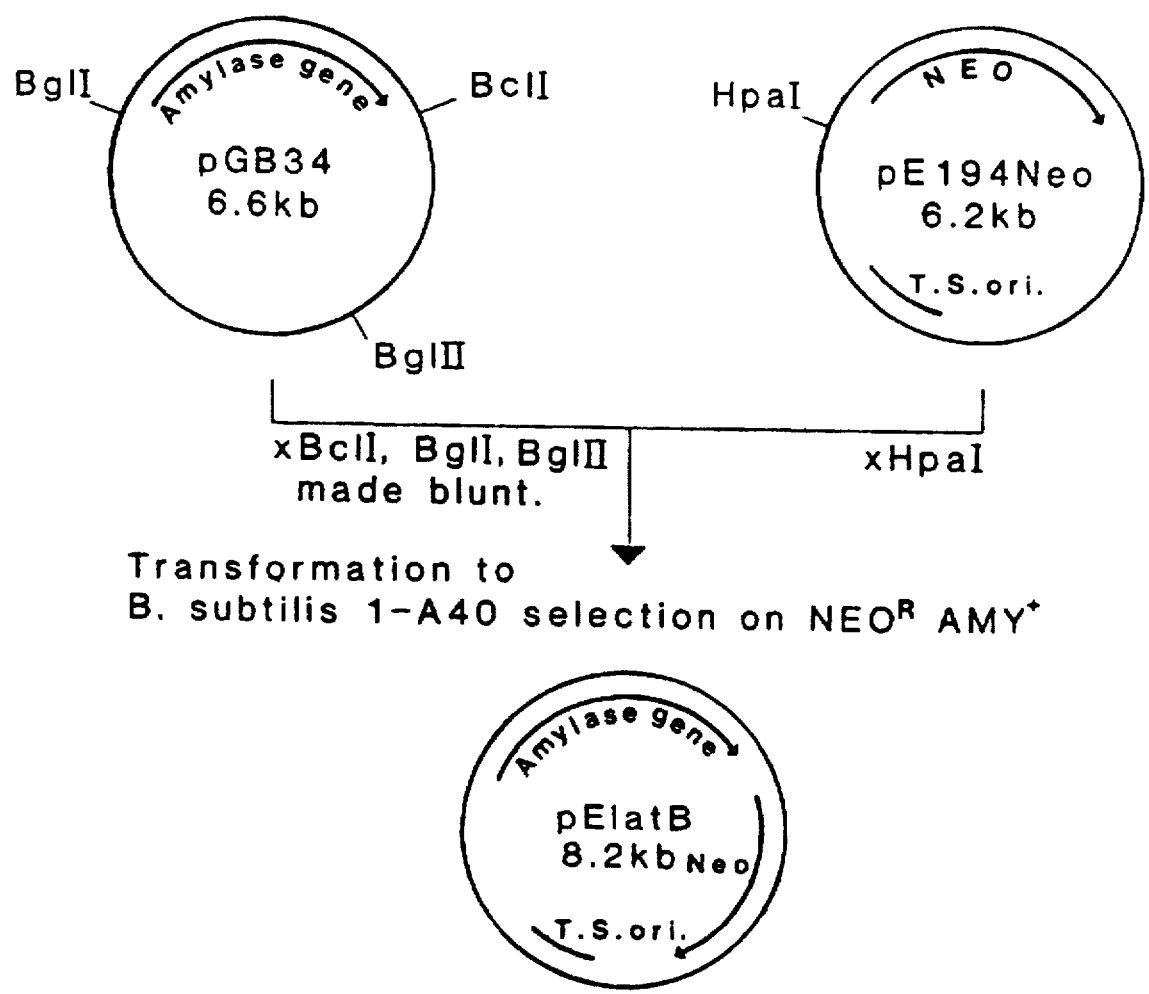

FIG. 8 shows the construction of integration vector pE1atB.

Figure 9A:
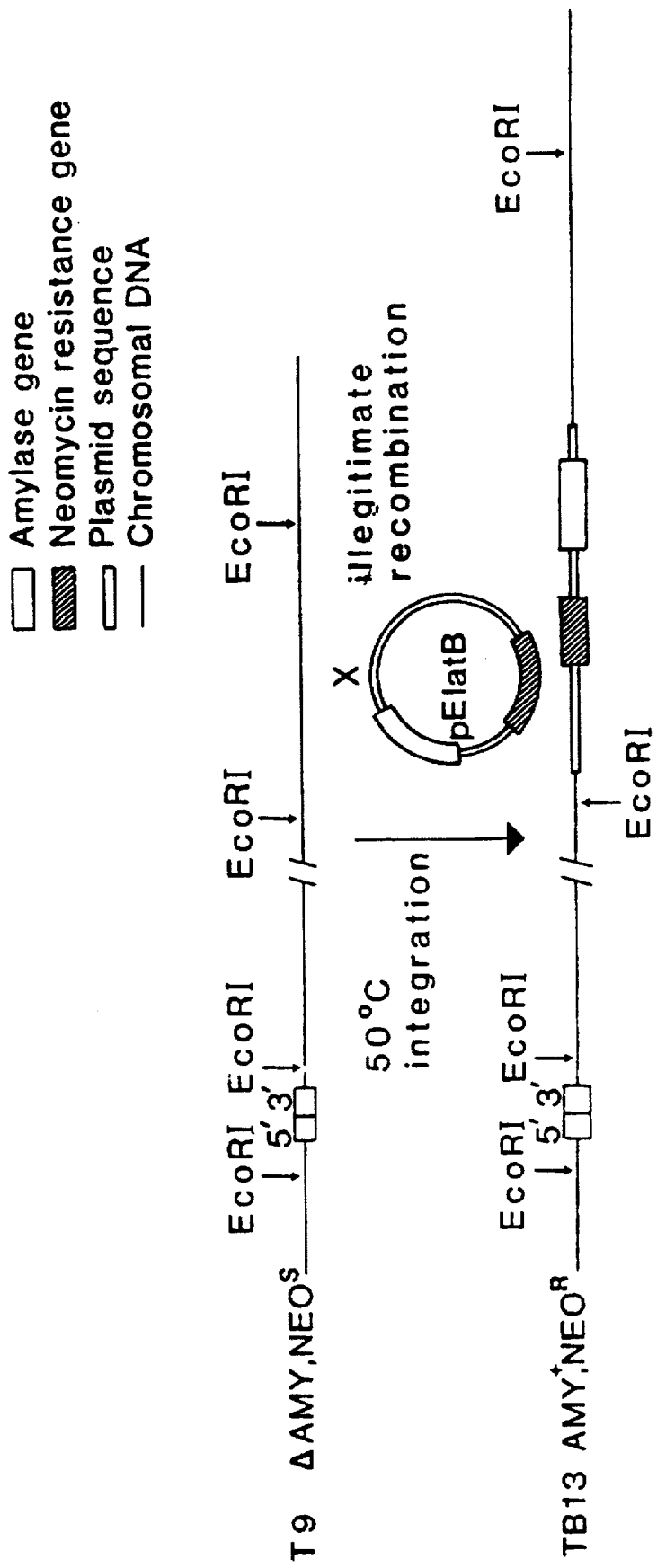

FIG. 9A illustrates the integration of plasmid pE1atB into the chromosome of *B. licheniformis* strain T9 resulting in *B. licheniformis* strain TB13.

Figure 9B:
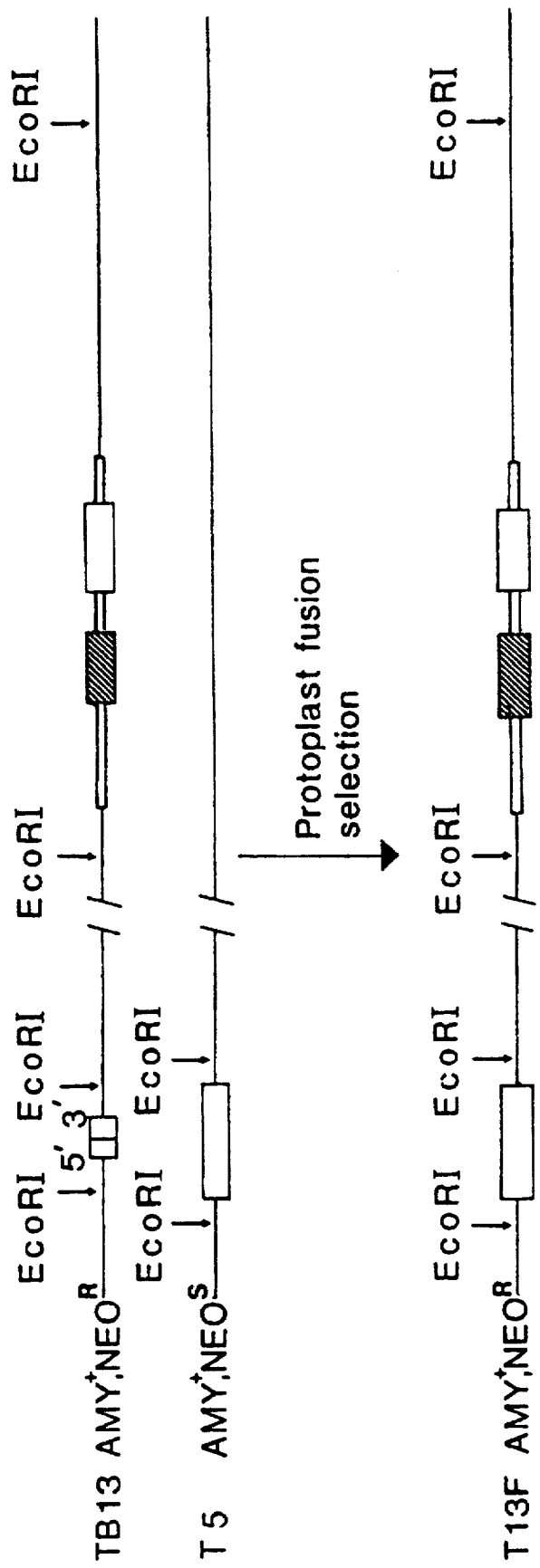

FIG. 9B illustrates the chromosomal recombination of the *B. licheniformis* strains TB13 and T5 upon protoplast fusion of these strains, resulting in *B. licheniformis* strain T13F.

Figure 10:
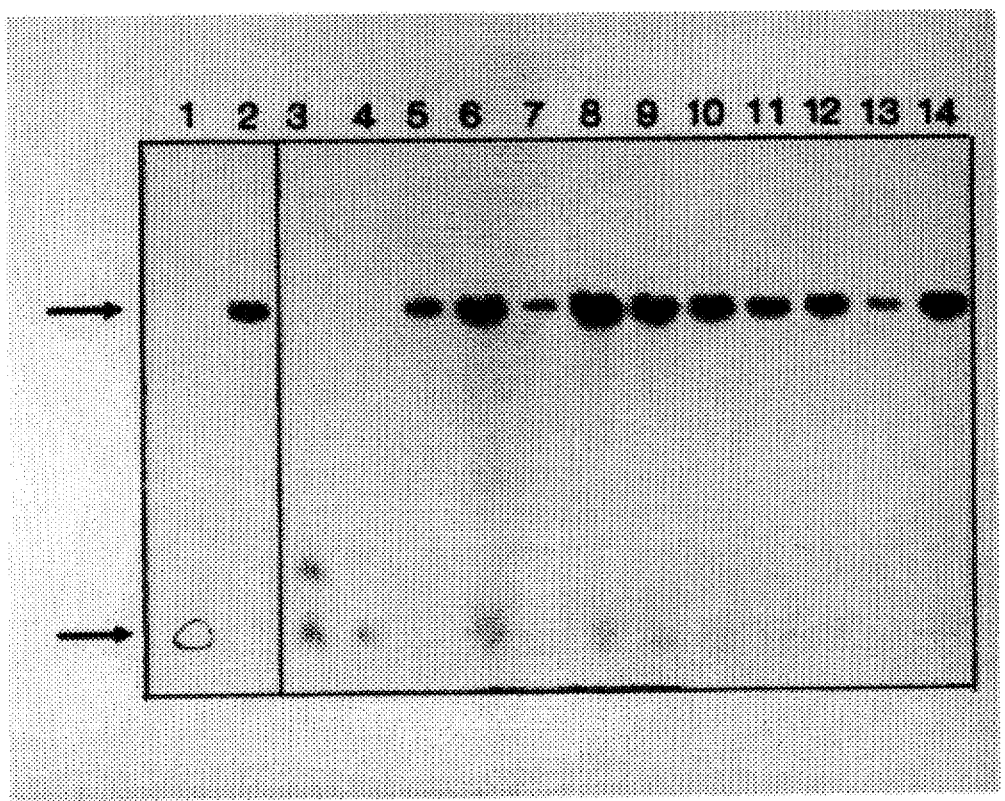

FIG. 10 shows a chromosomal analysis of nine different colonies isolated from a fermentation of strain T13F as described in Example 11. Isolated chromosomal DNA was digested with EcoRI separated on 0.8% agarose gels and blotted onto nitrocellulose. Hybridization of the blot was performed with $^{32}$P-labeled nick-translated pE1atB DNA. The figure shows an autoradiograph. The upper arrow indicates the position where an EcoRI DNA fragment of about 15 kb migrates which contains the entire pE1atB sequence that was integrated into the chromosome on a location not adjacent to the original α-amylase gene, as depicted for strain TB13 in FIG. 9A. The lower arrow indicates the position where an EcoRI DNA fragment of about 33 kb migrates which contains the entire α-amylase gene originally present in *B. licheniformis* strain T5 (see also FIG. 9B). The following DNA samples were analyzed:

Lane 1: *B. licheniformis* T5 DNA.

Lane 2: *B. licheniformis* TB13 DNA.

Lane 3: *B. licheniformis* T390 DNA.

Lane 4: DNA from a neomycin-sensitive derivative of *B. licheniformis* T390, isolated after fermentation, as described in Example 12.

Lane 5: *B. licheniformis* T13F DNA.

Lanes 6–14: DNA from nine different colonies isolated from a fermentation of strain T13F as described in Example 12.

DESCRIPTION OF THE SPECIFIC EMBODIMENTS

In accordance with the present invention, prokaryotic cells, and methods for their preparation, are provided in which two or more copies of a DNA sequence are stably integrated into the chromosome. A host cell comprising a DNA sequence encoding a polypeptide of interest is transformed with a DNA construct comprising said DNA sequence. Transformed cells in which the integrated DNA sequences are separated by endogenous chromosomal sequences from the gene to be amplified are then selected for. The endogenous intervening sequences are generally vital to the host cell. Loss of amplified sequences by homologous recombination will be lethal to the host cell. Thus, there will be selection pressure for cells carrying the amplified sequences without the necessity for using antibiotics or like selection means. Generally, the length of the intervening endogenous DNA sequences will be less than 10 kbp.

Figure 1A:
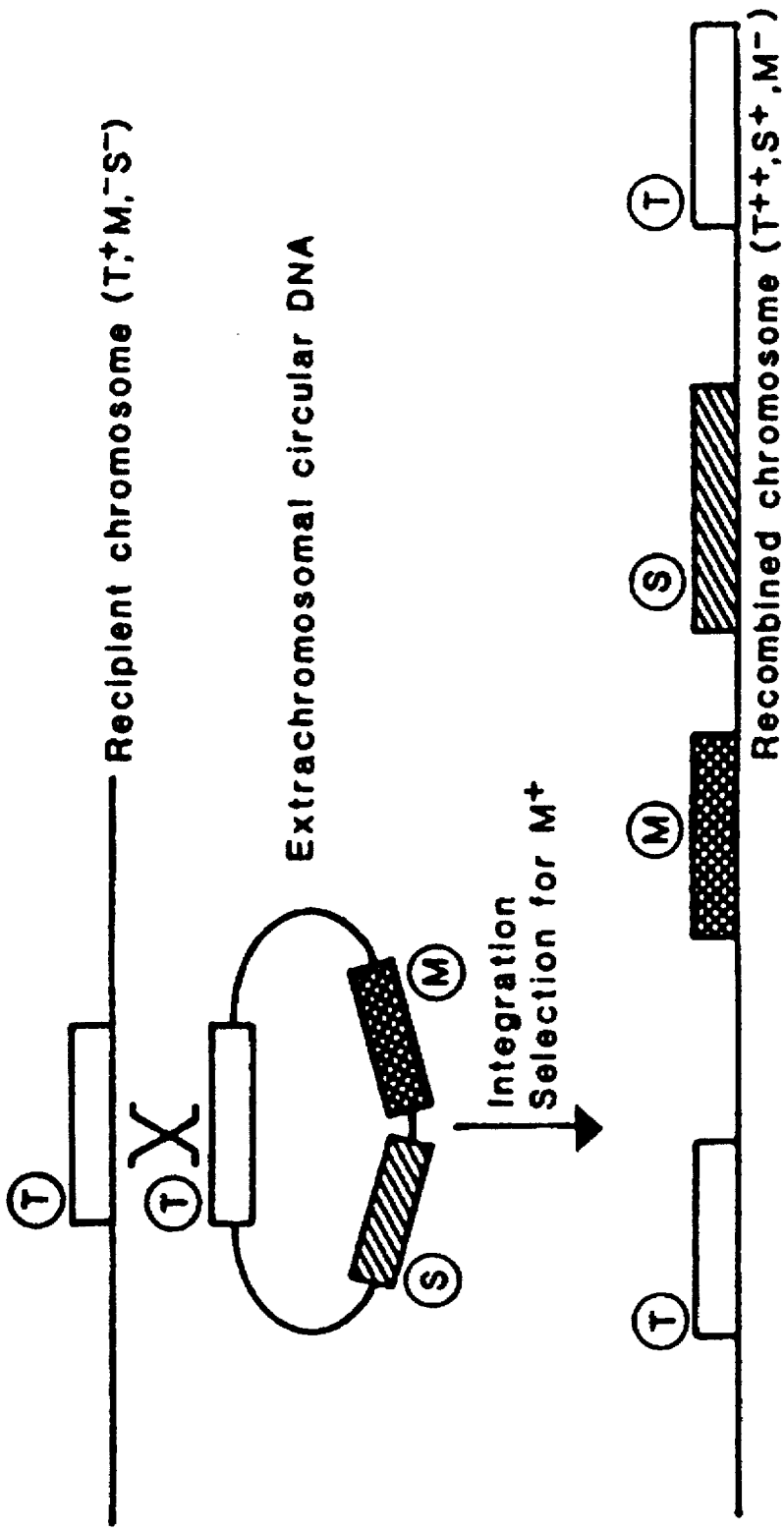
FIGS. 1A–D are schematic representations of four ways for integration of extrachromosomal DNA sequences into the chromosome of prokaryotic microorganisms.
Figure 1B:
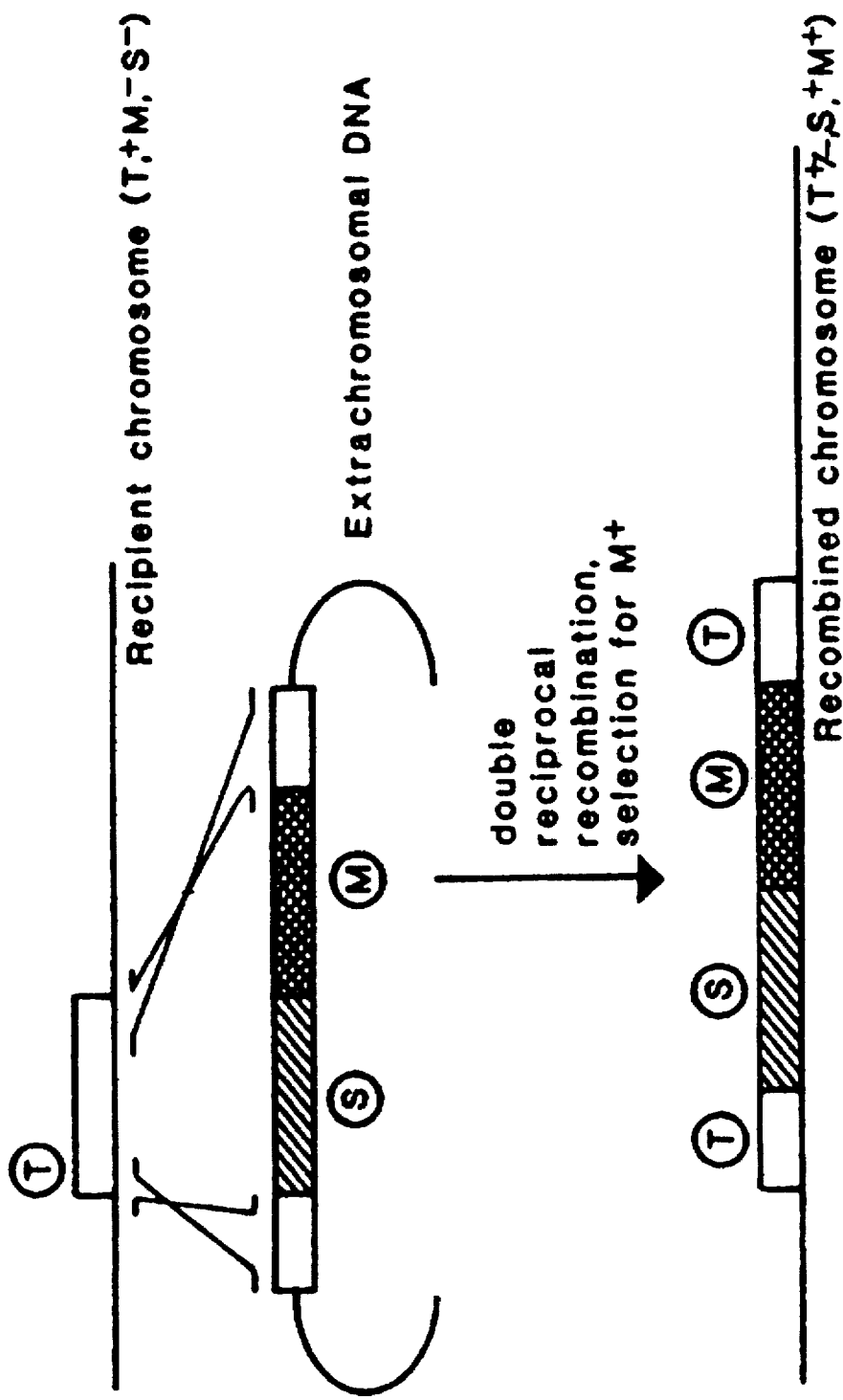
Figure 1C:
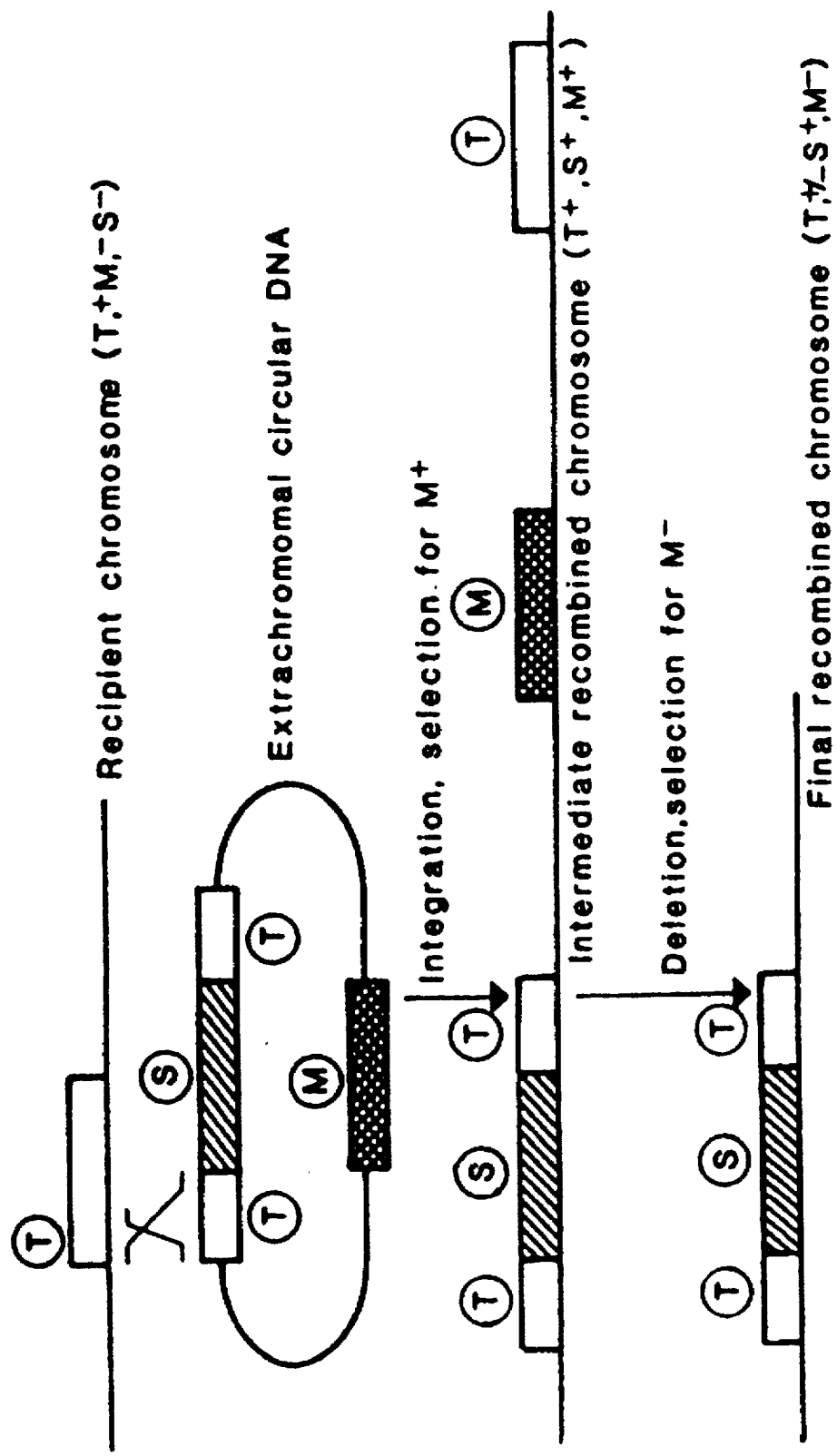
Figure 1D:
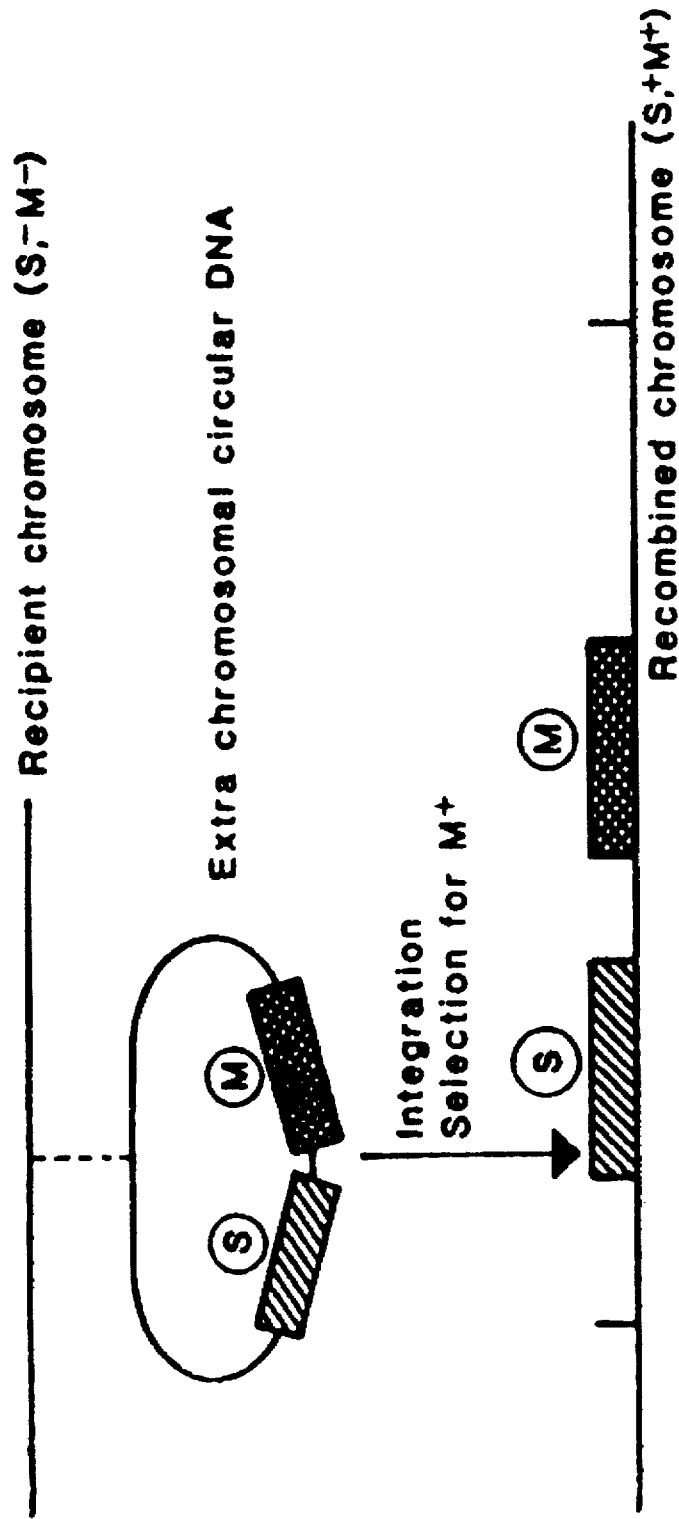

Several techniques can be used to obtain transformants having at least two copies of a gene of interest scattered in the transformant's chromosome. Examples of methods which can be used include those which avoid tandem integration, such as double reciprocal recombination as illustrated in FIGS. 1B and 2B. Several stretches of DNA sequences can be present in the vector molecules which are homologous to the host cell chromosome, especially when one or more copies of the gene to be amplified have already been introduced into the host cell. The vector molecule thus can include the DNA to be amplified; at least one target DNA sequence for recombination; and a marker DNA sequence.

Care has to be taken that only the desired recombined chromosomal arrangements are selected for. This can be achieved by using linear DNA molecules for recombination. The circular vector molecule to be integrated is cut with a restriction enzyme in the region homologous to the target sequence. In this way recombination and integration at this specific site can occur preferentially. In addition to being present in the vector molecule, the DNA sequence of interest can also be present in the host cell chromosome. The DNA sequence may be a DNA sequence encoding any structural gene which it is desired to amplify. The DNA sequence may be endogenous to the host organism, or may have been inserted into the host chromosome in a previous transformation step.

Target sequences for non-tandem gene amplification will preferably be chosen from among non-essential genes, for example in the case of Bacilli as host organisms, the genes encoding extracellular enzymes or genes involved in sporulation can be used as target sequences. Integration of DNA sequences in these genes will generally inactivate the gene. Loss of expression of the gene can then be monitored and used for the selection of the desired recombinant strains.

Other means for obtaining scattered gene transformants include the use of illegitimate recombination as illustrated in FIG. 2A. Isolation of tandem transformants can be avoided by selection using, for example, differential expression of a marker gene, for example a gene encoding antibiotic resistance, where sensitivity to the antibiotic is different in strains with tandem integration of the gene as opposed to non-tandem integration.

Scattered gene transformants can also be obtained by transforming first and second host cells which lack the structural gene of interest with a DNA construct comprising the structural gene, and a marker gene. First and second host cells in which the DNA sequence is present at different locations on the chromosome can then be selected and combined under fusing conditions to yield a transformed cell (acceptor strain) with at least two copies of the DNA sequence encoding the polypeptide of interest at scattered locations in its genome. For ease of selection the first host (donor host) can be killed prior to fusion.

Depending upon the method of transformation used, a mixture of transformants having the genes of interest integrated in tandem array and those transformants having the genes of interest scattered in the chromosome, may be obtained. When a mixture of transformants is obtained, those containing scattered genes can be selected from the mixture by isolating chromosomal DNA from each individual transformant, and analyzing the isolated DNA with respect to the relative locations of the inserted genes by, for example, the method of Southern, *J. Mol. Biol.* (1975) 98:503–517 or other means known to those skilled in the art. Transformants having scattered integration of the genes of interest are thereby identified.

The gene(s) of interest may be any prokaryotic or eukaryotic gene. These genes may include bacterial genes, unicellular microorganism genes, mammalian genes, or the like. The structural genes may be prepared in a variety of ways, including synthesis, isolation from genomic DNA, preparation from cDNA, or combinations thereof. The various techniques of manipulation of the genes are well-known, and include restriction, digestion, resection, ligation, in vitro mutagenesis, primer repair, employing linkers and adapters, and the like. Thus, DNA sequences obtained from a host may be manipulated in a variety of ways, depending upon the requirements of the DNA construction. See Maniatis et al., *Molecular Cloning*, Cold Spring Harbor Laboratory, Cold Spring Harbor, N.Y., 1982.

The structural genes may express a variety of polypeptides or proteins, such as enzymes, hormones, lymphokines, surface proteins, blood proteins, structural proteins, immunoglobulins, or the like, from mammals, unicellular microorganisms, e.g., bacteria, fungi, such as yeast, or filamentous fungi, algae, protozoa, etc., plants, or other DNA source. Of particular interest are enzymes, more particularly proteases and amylases. Illustrative of such enzymes are serine and non-serine proteases including high alkaline serine proteases, α- and β-amylase, and the like. A preferred source for a serine protease is Bacillus novo species PB92, and for an alpha amylase is *B. licheniformis* strain T5, as well as variants and mutants of these strains.

The gene that forms part of the suitable vector can be obtained by methods generally known in the art. Generally, the method comprises preparing a genomic library from the organism expressing the polypeptide of interest. The genomic library is conveniently prepared for example by ligating DNA fragments of the donor strain into a suitable vector.

By the term "suitable vector" is meant a DNA construct comprising a structural gene encoding a protein or polypeptide of interest, in particular an enzyme. The structural gene is joined in proper orientation to control regions such as a promoter sequence, a sequence forming the ribosome binding site and sequences controlling termination of transcription and translation of the structural gene, which control regions are functional in the host cell. Where the host cell has transformation and integration frequencies which are too low to permit direct selection for integration without intermediate isolation of plasmid containing cells, such as industrial Bacillus strains, the vector can additionally comprise an origin of replication that is capable of replicating autonomously in the host cell.

Where the gene is obtained from a donor cell which has transcriptional and translational initiation and termination regulatory signals which are recognized by the host prokaryotic cell strain, it will usually be convenient to maintain the original regulatory sequences of the structural gene. In addition, the transcriptional initiation region may provide for constitutive or inducible expression, so that in appropriate situations, the host may be grown to high density before high levels of expression of the structural genes of interest are obtained.

Where the structural gene is from a source whose regulatory signals are not recognized by the host cell, it will be necessary to obtain regulatory regions recognized by the host cell and to insert the structural gene between the initiation and termination regulatory signals. In some instances the exogenous structural gene with its own stop codon(s) may be inserted in reading frame behind the N-terminus codons of an endogenous structural gene which retains its natural regulatory signals.

It is desirable that the expression product be secreted. Where the expression product is naturally secreted and the leader signals and processing signal(s) are recognized by the host cell, this will entail no difficulty. However, where the product is not secreted because the host cell does not recognize the secretory leader signals and/or processing signal(s), or the signals are not functional to a satisfactory degree in the host cell, then it may be necessary to isolate or synthesize DNA sequences coding for the secretory leader signals and processing signal(s) of a host cell polypeptide and join them in proper reading frame to the 5'-end of the structural gene.

The vector may additionally include a marker gene conferring resistance to an antibiotic to which the host strain is sensitive. The marker gene, when used in chromosomal integration of the vector, has to fulfill the demand that survival selection is possible even if only one or a few copies of the marker gene are present in the host strain. By marker is intended a structural gene capable of expression in a host, which provides for survival selection. By "survival selection" is intended imparting prototrophy to an auxotrophic host, biocide or vital resistance. For prototrophy, various genes may be employed, such as leu, his, trp, or the like. For biocide resistance this may include resistance to antibiotics, e.g., neo, cam, tet, tun, kan, or the like. Other markers include resistance to heavy metals, immunity, and the like. The various DNA sequences may be derived from diverse sources and joined together to provide for a vector which includes one or more convenient, preferably unique, restriction sites to allow for insertion or substitution of the structural genes at such sites or in place of lost fragments to provide the plasmid construct.

Selection for chromosomal integration may be aided by using a plasmid with an origin of replication having a mutation which makes its functioning temperature-sensitive in the host cell. See, for example, Ehrlich, *Proc. Natl. Acad. Sci. USA* (1978) 75:1433.

Once the plasmid construct has been prepared, it may now be cloned in an appropriate cloning host. Any host may be used which is convenient, is readily transformable, and allows for replication of the plasmid construct and transfer to the host cell. A large number of strains are available which have a high efficiency of transformation and are usually auxotrophic and/or antibiotic sensitive. Where the host cell is an industrial Bacillus strain, the use of the same organism as the host cell for cloning of the plasmid construct has many advantages in that it permits the use of a single replication system as well as the same marker for survival selection in both the cloning host and the host strain. See, for example, European application EP-A-0134048, which disclosure is incorporated herein by reference.

The plasmid construct may be introduced into the cloning host in accordance with conventional techniques, such as transformation, employing calcium precipitated DNA, conjugation, or other convenient technique. The cloning host may then be grown in an appropriate nutrient medium, under selective conditions to select for a host containing the plasmid construct. For auxotrophic hosts, the nutrient medium is deficient in the required nutrient, while for biocide resistance, e.g., antibiotic resistance, a cytotoxic amount of the biocide(s) is employed in the nutrient medium.

Various host cells may be employed. These include *E. coli*, Bacillus strains, especially *B. subtilis*, Pseudomonas, and Streptomyces. In choosing a host cell, various factors are taken into account, including factors which can affect expression of the gene to be amplified and production of the desired product. Thus it is desirable to use a host cell in which there is recognition of regulatory signals; ease of secretion; reduced degradation of the desired product, etc. A preferred host cell already produces the polypeptide of interest, and may be either a wild type organism or a mutant organism. The host cell can also be a mutant of an organism which produces the polypeptide of interest which itself, however, is a non-producer. Where the polypeptide of interest is a protease or an amylase, preferred strains include Bacillus novo species PB92 and *B. licheniformis* strain T5 respectively, as well as mutants and variants of these strains.

In addition, host strains may be employed which have the desired traits of an industrial strain. Examples of strains which may be employed include strains used for the industrial production of enzymes such as: *B. licheniformis, B. amyloliquefaciens* and alkalophilic bacilli. The industrial strains are chosen from organisms which may be isolated in the soil or available from depositories or other sources or obtained by modification of such strains. The industrial strains are highly robust and stable. Furthermore, such strains are resistant to phage infection and to genetic exchange, that is introduction of DNA by conventional transformation procedures. The conventional industrial strains are also prototrophic, in order to avoid adding expensive amino acids to the nutrient medium. Other characteristics of industrial stains are their high productivity until the end of the fermentation, which can be as long as a week, stable cell concentration upon exhaustion of the broth, and high productivity, usually at least 5 g/l (0.5% w/v) of a specific secreted protein.

Transformation of the host cells preferably involves the use of protoplasts prepared from the host strain. Protoplasts generally are prepared from the host cells in accordance with conventional ways, e.g., lysozyme or zymolyase treatment, and the protoplasts carefully suspended in an appropriate medium having proper osmolality for maintaining the integrity of the protoplast. For industrial Bacillus strains, methods for preparing protoplasts are described in European Application No. EP-A-0134048, which disclosure is incorporated herein by reference. Where the host strain is an alkalophilic Bacillus strain, protoplasts may conveniently be prepared at alkaline pH, preferably about pH 8.0. This procedure is disclosed in European Application No. EP-A-87200358.7, which disclosure is incorporated herein by reference.

The host cell can be transformed by combining the plasmid construct or a cloning host protoplast with the host cell protoplast in the presence of an appropriate fusogen. Any fusogen may be employed which provides the desired degree of efficiency. For the most part, polyethylene glycol is found to provide high efficiency of fusion with great convenience. After a short time, the fusogen mixture is replaced with an appropriate nutrient medium and cells regenerated in a selective medium, conveniently by plating on an agar plate.

Transformants obtained by combining a host cell with a suitable DNA construct can contain a DNA construct or part thereof either directly as an integral part of the chromosome or as a free vector molecule when the DNA construct contains an origin of replication functional in the host cell. To select for transformants which have the DNA construct integrated into the chromosome, a plasmid containing a temperature-sensitive origin of replication can be used. Transformants are grown in a selective medium at the permissive temperature, then shifted to a non-permissive temperature. Colonies expressing the marker gene at the non-permissive temperature are then isolated and cultured in selective medium at the permissive temperature. Plasmid absence can be verified, for example by isolating total DNA from the colonies and electrophoresing on an agarose gel or by demonstrating lack of ability of the transformants to transform competent cells. Determination of the way in which integration into the chromosome has taken place can be by analysis of the chromosomal DNA by, for example, the method of Southern, supra., or other methods known to those skilled in the art.

When there is a differential sensitivity to the selective agent between transformants containing additional copies of the marker gene in a tandem array as compared to those in which the marker gene is incorporated at scattered locations in the host genome, transformants can conveniently be grown in medium containing the appropriate concentration of selective agent to select for transformants with non-tandem integration.

Another means of obtaining transformants with scattered integration of copies of the DNA sequence of interest is to use a protoplast prepared from an homologous donor cell, containing at least one copy of the DNA sequence of interest at a location on its chromosome different from that of the recipient host cell. The homologous donor cell can be prepared, for example, by transforming a cell which does not contain the structural gene of interest with a vector comprising the structural gene. Integration of the DNA sequence into the donor cell chromosome can be facilitated by using a plasmid containing a temperature-sensitive origin of replication and growing transformants under selective conditions first at the permissive temperature and then at the non-permissive temperature as described above, then isolating colonies expressing the marker gene.

Following verification of the absence of plasmid DNA, the chromosomal DNA can be isolated and analyzed according to the method of Southern, supra, by hybridizing with a probe labeled with, for example, $^{32}P$ or biotinylated nucleotides. The probe may be cDNA encoding the polypeptide of interest or fragments thereof as well as DNA constructs or fragments thereof comprising the DNA sequence of interest, for example a vector. Transformants containing the gene of interest at an alternate location as compared to that of the gene donor strain can then be used as an homologous donor cell. The recipient strain host is preferably the same as the strain used as the source of the DNA sequence of interest, or a strain in which the DNA sequence of interest is located at a different region of the chromosome than in the transformed donor cell.

To aid in selection, the donor cell preferably is killed with a cytotoxic agent prior to or during protoplast formation. Various agents may be employed to kill the donor cell, including antibiotics, but iodoacetamide is found to be convenient, efficient, and does not interfere with the subsequent fusion. When dead cloning host protoplasts are used, the ratio of the dead protoplast to the acceptor strain host will be preferably at least about 1:1 and an excess of the dead protoplast may be employed.

Following fusion of the dead donor cell protoplast and the recipient host cell protoplast, transformants can be selected by means of the marker gene. DNA can then be isolated and analyzed as described above to identify transformants in which more than one copy of the gene of interest has been incorporated into the genome and are separated by endogenous chromosomal sequences.

Scattered two-gene transformants are then screened in appropriate ways for detection of increased expression of the polypeptide of interest. Various techniques may be employed, particularly where enzymes are involved which have well established methods of detection. Alternatively, where enzymes are not involved or there is no available detection system, bioassays, antibodies, restriction analysis, or DNA or RNA hybridization can be employed for screening the clones to determine the presence of the plasmid construct and expression of the structural gene of interest.

The host cell containing the chromosomally integrated plasmid constructs or fragments thereof is then grown in a nutrient medium under conventional fermenting conditions. The fermenting may be continued until the broth is exhausted. Where the product has been secreted, the product may be isolated from the broth by conventional techniques, e.g., extraction, chromatography, electrophoresis, or the like.

Where the product is retained in the cytoplasm, the cells may be harvested by centrifugation, filtration, etc., lysed by mechanical shearing detergent, lysozyme, or other techniques and the product isolated as described previously.

The following examples are offered by way of illustration and not by way of limitation.

EXPERIMENTAL

EXAMPLE 1

Preparation of a Genomic DNA Library from Alkalophilic Bacillus novo sp. PB92 and Isolation of the Serine Protease Gene Chromosomal DNA was isolated from Bacillus novo sp. PB92 deposited at the American Type Culture Collection (ATCC) 12301 Parklawn Drive, Rockville, Md. 20852 on May 8, 1978 under ATCC Accession Number 31408 and deposited under No. OR-60 with Laboratorium voor Microbiologic, Technical University of Delft, the Netherlands, see U.S. Pat. No. Re. 30,602) according to the procedure described by Saito-Miuva, *Biochim. Biophys. Acta* (1963) 72:619–632. The DNA was partially digested with the restriction enzyme Sau3A and ligated into the BamHI site of plasmid pUB110 (Gryczan et al., *J. Bacteriol.* (1978) 134:318–329). pUB110 plasmid DNA was prepared as described by Birnboim and Doly (*Nucleic Acids Res.* (1979) 7:1513–1523).

The ligation mixture was transformed into *B. subtilis* 1A40 (Bacillus Genetic Stock Center) according to the method of Spizizen et al., *J. Bacteriol.* (1961) 81:741–746, using 0.6–1 µg DNA per ml of competent cells. Cells from the transformation mixture were plated on minimal plates containing: 2.8% $K_2HPO_4$, 1.2% $KH_2PO_4$, 0.4% $(NH_4)_2SO_4$, 0.2% tri-Na-citrate.$2H_2O$, 0.04% $MgSO_4.7H_2O$, 0.00005% $MnSO_4.4H_2O$, 0.4% L-glutamic acid, 0.5% glucose, 0.02% casamino acids, 50 µg/ml tryptophan, 20 µg/ml methionine, 20 µg/ml lysine, 20 µg/ml neomycin, 0.4% casein and 1.5% agar. After overnight incubation of the plates at 37° C., one out of 50,000 neomycin resistant colonies showed increased protease production, as determined by increased precipitation of a halo of casein cleavage products around the colony in the agar plate. Plasmid DNA was isolated from this colony according to the method described by Birnboim and Doly, *Nucleic Acids Res.* (1979) 7:1513–1523, and named pM58.

EXAMPLE 2

Expression of the PB92 Serine Protease Gene

*Bacillus subtilis* 1A40 containing pM58 was grown in minimal medium (Spizizen et al., *Proc. Natl. Acad. Sci. USA* (1958) 44:1072–1078) to which had been added 0.02% casamino acids, 50 µg/ml tryptophan, 20 µg/ml methionine, 20 µg/ml lysine and 20 µg/ml neomycin. After 24 hours, the culture was centrifuged and the supernatant assayed for protease activity using dimethyl casein as substrate (Lin et al., *J. Biol. Chem.* (1969) 244:789–793. A control culture of *B. subtilis* 1A40 containing the plasmid pUB110 showed less than 1/60 of the protease activity shown by the pM58 transformed culture. Protease activity was completely inhibited by treatment with 1 mM phenylsulfonyl fluoride (PMSF), but not by treatment with 20 mM EDTA.

Aliquots of the above described supernatants were analyzed on protein gels according to the method of Laemmli, *Nature* (1970) 227:680. Samples for analysis on these gels were prepared by treatment of the supernatants with 5% trichloroacetic acid (TCA). Following centrifugation of the sample, the pellet of precipitated protein was washed twice with acetone then dissolved in 40 µl sample buffer (0.5M Tris/HCl, pH 7.5, 10% v/v 2-mercaptoethanol, 50% v/v glycerol and 0.05% Bromophenol Blue) by boiling fop 10 minutes. Culture supernatant samples were then analyzed by electrophoresis. Three different *B. subtilis* 1A40 strains were used: a strain containing pUB110; pM58 and no plasmid, and Bacillus PB92 protease as a control. After electrophoresis, the gels were stained using Coomassie Brilliant Blue and destained. The sample from *B. subtilis* strain 1A40 containing pM58 contained a 31 kD protein, which comigrates with Bacillus PB92 protease. This protein was not detected on the control lane of strain *B. subtilis* 1A40 containing pUB110.

All serine proteases have similar molecular weights. The cloned serine protease of Bacillus PB92 therefore was differentiated from known serine proteases (*B. subtilis* subtilisin, Carlsberg subtilisin), by transformation of pM58 and pUBS10 to the protease negative *B. subtilis* strain DB104 (Doi, *J. Bacteriol.* (1984) 160:442–444) and analysis of the extracellular proteases produced. The obtained transformants were grown in minimal medium (Spizizen et al., *Proc. Natl. Acad. Sci. USA* (1958) 44:1072–1078) containing 0.02% casamino acids, 50 µg/ml histidine and 20 µg/ml neomycin. After 24 hours, samples were taken, centrifuged and without pretreatment analyzed on histidine/MOPS gels containing 75 mM KOH, 40 mM histidine, 100 mM MOPS (3-(N-morpholino)-propanesulfonic acid), pH 7.5 and 5% polyacrylamide. Electrophoresis buffer contained 40 mM histidine, 100 mM MOPS, pH 6.6. Samples were run in the direction of the cathode. Protease bands were detected with Agfa Pan 100 Professional films (Zuidweg et al., *Biotechnol. and Bioengin.* (1972) 14:685–714). These results are shown in FIG. 3. As shown in FIG. 4, pM58 harbors the gene encoding Bacillus PB92 protease.

EXAMPLE 3

Sequencing of the Bacillus novo species PB92 Serine Protease Gene

The entire sequence of a BalI-HpaI fragment of pM58 was determined by the method of Sanger, *Proc. Natl. Acad. Sci. USA* (1977) 74:6463. Restriction fragments of pM58 (see FIG. 4) were cloned in phase M13 vectors mp10, mp11 and mp18 (Messing et al., *Nucleic Acids Res.* (1981) 9:309–321. Insertions of pM58 fragments were screened by plaque hybridization. After sequencing, ten oligonucleotides located at regular distances on the gene were made and sequencing was repeated, confirming the sequence shown in FIG. 5.

EXAMPLE 4

Construction of Serine Protease Containing Plasmid pMAX-4

To construct plasmid pUCN710 (FIG. 6A) pUB110 was digested with TaqI and PvuII. The fragment containing the gene conferring neomycin resistance was purified on low melting agarose and made blunt with Klenow polymerase and NTP's (Maniatis, *Molecular Cloning: A Laboratory Manual*, Cold Spring Harbor 1982). Plasmid pUC7 (Vieira et al., *Gene* (1982) 19:259–268) was linearized with SalI and made blunt as described above. Both fragments were ligated with T4 ligase (Maniatis) and transformed to JM103. Selection took place on 2xTY plate (1.6% w/v Bacto-trypton, 1% w/v yeast extract, 0.5% NaCl) containing 50 µg/ml ampicillin and 10 µg/ml neomycin. The resulting plasmid, named pUCN710, was digested with BamHI. The plasmid pE194 (Jordanescu, *Plasmid* (1978) 1:468–479) was digested with BclI. The fragments from both digestions were ligated with T4 ligase and transformed to *B. subtilis*-1A40. Selection took place on minimal plates containing 20 µg/ml neomycin (see Example 1). The plasmid obtained, pE194-neo (FIG. 6A), contains the neomycin gene and a temperature sensitive origin of replication.

Subcloning of the protease gene in integration vector pE194-neo was performed as follows: pM58 (see Example 1) was digested with HpaI, BalI and BglII. Plasmid pE194-neo was digested with HpaI. These fragments were ligated with T4 ligase and transformed to B. subtilis 1A40. Transformants were selected based upon neomycin resistance and an increase in protease production, as judged by casein cleavage products precipitation (halo formation, see Example 1). Plasmid pMAX-4 was obtained, the structure of which was confirmed by restriction enzyme analysis (see FIG. 6B).

EXAMPLE 5

Protoplast Transformation of Bacillus novo strain PB92 by pMAX-4

Bacillus strain PB92 was grown overnight in 100 ml NBSG-X medium (Thorne et al., J. Bacteriol. (1966) 91:1012–1020). The culture was centrifuged for 10 minutes at 4,500 rpm in a Sorvall model GSA rotor. Protoplasts were prepared by incubating the bacilli for one hour at 37° C. in 10 ml Alkaline Holding Medium (AHM) containing 0.5M sucrose, 0.02M $MgCl_2$ and 0.02M Tris/maleate, pH 8.0, in sterile water to which 0.4 mg/ml lysozyme was added. The protoplasts were pelleted (10 minutes at 4,500 rpm), resuspended in 5 ml $AHM^+$ pH 8.0 buffer (AHM buffer to which 3.5% w/v Bacto Penassay Broth and 0.04% w/v Albumine Merieux had been added) mixed, then pelleted as above.

After being resuspended in 5.0 ml of alkaline holding medium, 0.5 ml of this suspension of protoplasts were mixed with 5 µl of demineralized water containing 1 µg of plasmid DNA and incubated for 2 minutes in the presence of 30% w/v polyethylene glycol 8,000, pH 8.0. After 1:3 dilution with $AHM^+$ pH 8.0 medium and centrifugation, the pellet was resuspended in a small volume (1 ml) of $AHM^+$ and incubated for 2–3 hours. One hundred microliter aliquots were plated on freshly prepared regeneration plates containing 0.5M Na succinate/HCl pH 8.0, 1.5% w/v agar, 0.5% w/v casamino acids, 0.5% w/v yeast extract, 0.031M phosphate buffer pH 8.0, 0.5% w/v glucose, 0.02M $MgCl_2$ and 0.02% w/v Albumine Merieux. These plates also contained 1 mg/ml neomycin for selection. After incubation at 37° C. for at least 72 hours, the colonies were replica-plated onto heart infusion agar plates containing 20 µg/ml neomycin.

EXAMPLE 6

Integration of pMAX-4 in the Bacillus Strain PB92 Chromosome

A transformant of Bacillus PB92 containing plasmid pMAX-4, was incubated in Tryprone Soya Broth (TSB) containing either 1 µg/ml or 20 µg/ml neomycin for 24 hrs at 37° C. Two ml portions of the cell suspensions were then diluted in 100 ml of TSB containing 1 µg/ml or 20 µg/ml neomycin, respectively, and incubated for 24 hrs at 50° C. After 24 hrs 5 ml samples of both cultures were dilated again, as described above, and incubated for 24 hrs at 50° C., again in the presence of 1 µg/ml or 20 µg/ml neomycin, respectively. The last procedure was repeated once more. The cell suspensions were then diluted 100-fold aid plated on Heart Infusion (HI) agar plates containing 1 µg/ml neomycin for the samples from the flasks containing 1 µg/ml neomycin, and 20 µg/ml neomycin for the samples from the flasks containing 20 µg/ml neomycin. The plates were incubated for 16 hrs at 50° C. Neomycin-resistant colonies were isolated and cultured in 10 ml TSB medium containing 1 µg/ml neomycin for 16 hrs at 37° C. From these cultures total DNA was isolated (Holmes et al., Anal. Biochem. (1981) 114:193–197). Plasmid absence was verified by DNA electrophoresis on agarose gel. Absence of plasmid DNA from samples in which plasmid DNA was not detectable was confirmed by transformation of total DNA to B. subtilis 1A40. Samples lacking the ability to transform B. subtilis 1A40 were considered plasmid-free.

To check whether and in what way integration of pMAX-4 in the chromosome took place, chromosomal DNA was isolated, digested with HindIII, run on 0.5% DNA agarose gels and blotted to nitrecellulose (Southern, J. Mol. Biol. (1975) 98:503–517), and hybridized with $^{32}P$-labeled nick-translated pM58 (Maniatis, Molecular Cloning: A Laboratory Manual, 1982, Cold Spring Harbor). The result of this analysis is shown in FIG. 7A.

Selection at 1 µg/ml neomycin resulted in protease genes tandemly located in the chromosome and separated by plasmid sequences (strain PBT109) as a result of homologous recombination (Campbell-type mechanism). In an accumulation of 30 independently isolated integrants, selection was performed at 1 µg/ml neomycin. One integrant was isolated which contained the plasmid pMAX-4 on a random location in the chromosome as a result of an illegitimate recombination (strain PBT122). Selection at 20 µg/ml neomycin resulted in a copy of a plasmid pMAX-4 on a random location in the chromosome as a result of an illegitimate-type recombination. The latter strain was named PBT108. The genetic organization of strains PBT109 and 108 are depicted in FIGS. 7B and 7C, respectively. Chromosomal analysis showed that integration in PBT122 and PBT108 occurred on different locations in the chromosome.

EXAMPLE 7

Stability of Duplicated Protease Genes in Strains PBT108 and PBT109

One hundred ml of production medium (1% starch, 4% lactose, 0.87% $K_2HPO_4$, 0.5% yeast extract, 0.5% $(NH_4)_2HPO_4$, 0.2% Tri Na citrate.$2H_2O$, 0.05% $MgSO_4.7H_2O$, 0.07% $CaCl_2$, 0.068% $FeSO_4.7H_2O$ and antifoam 1 ml/l) without neomycin was inoculated with 0.2 ml of an overnight TSB culture (37° C.) of strain PBT108 or PBT109 in 500 ml shake flasks. After incubation for 44 hrs at 37° C. under constant aeration the culture was tested for neomycin-resistant colonies and for protease activity.

Both strains PBT108 and PBT109 were also tested in Eschweiler fermenters into the same production medium to check the effect of upscaling to 10 l. The results of the fermentation experiments are summarized in the following table.

TABLE 1

| Strain | Relative Production of Protease* | Percent of Neomycin-Resistant Cells After Fermentation |
| --- | --- | --- |
| Control (PB92) | 100% | — |
| PBT108 | 120% | 100% |
| PBT109 | 115–120% | 75–97% |

*Protease activity was assayed using dimethylcasein as substrate as described by Lin et al., J. Biol. Chem. (1969) 244:789–793.

Analysis of colonies derived from the Eschweiler fermentation of PBT109 after 2 days of culturing, showed that 3–25% of these colonies produced at the level of a strain containing only a single protease gene. These same colonies were neomycin-sensitive due to excission of the pMAX-4 sequence by homologous recombination. However, analysis of the colonies derived from the strain PBT108 fermentation experiment showed that these cells were all neomycin-resistant. One hundred of these neomycin-resistant colonies were taken at random and individually tested for protease production potential, to determine whether they contained one or two productive protease genes. All 100 individually tested colonies produced at the level of a strain containing two genes, showing that the two randomly integrated protease genes in PBT108 are stably maintained under the fermentation conditions used.

EXAMPLE 8

Construction of Integration Vector pElatB

Plasmid pGB34, described in EP-A-0134048, was digested with the restriction enzymes BclI, BglI and BglII. The restriction fragments obtained were blunt-ended with Klenow polymerase, then were ligated into the HpaI site of pE194neo (see Example 6). Plasmid pE194neo DNA was isolated as described by Birnboim and Doly, Nucl. Acids Res. (1979) 7:1513–1523.

The ligation mixture was transformed into B. subtilis 1-A40, according to the method of Spizizen et al., J. Bacteriol. (1961) 81:741–746, using 0.5 to 1 µg DNA/ml of competent cells. Cells from the transformation mixture were plated on minimal plates containing 2.8% $K_2HPO_4$, 1.2% $KH_2PO_4$, 0.4% $(NH_4)_2SO_4$, 0.2% Tri Na citrate.$2H_2O$, 0.04% $MgSO_4.7H_2O$, 0.00005% $MnSO_4.4H_2O$, 0.4% glutamic acid, 0.5% glucose, 0.02% casamino acids, 50 µg/ml tryptophan, 20 µg/ml methionine, 20 µg/ml lysine, 20 µg/ml neomycin, 0.4% casein, 0.5% starch and 1.5% agar.

DNA of α-amylase producing colonies was isolated as described by Birnboim and Doly and checked with restriction enzymes. From one of these transformants plasmid pElatB, see FIG. 8, was isolated.

EXAMPLE 9

Transformation of the α-amylase Negative Strain Bacillus licheniformis T9 with pElatB Transformation of B. licheniformis strain T9 was carried out as described in EP-A-0253455 with the exception that the entire procedure was performed at 30° C. instead of at 37° C. Selection for transformants was carried out on minimal plates containing 20 µg/ml neomycin. All transformants produced amylase. Restriction enzyme analysis performed on DNA prepared as described by Birnboim and Doly showed that the transformants all contained pElatB.

EXAMPLE 10

Integration of pElatB into the B. licheniformis T9 Chromosome

Bacillus licheniformis strain T9 containing plasmid pElatB, was inoculated in Tryptone Soya Broth (TSB) containing 20 µg/ml neomycin and incubated for 16 hours at 30° C. A 5 ml portion of the cell suspension was then diluted in 100 ml of the same medium and incubated at 50° C. for 24 hours.

This procedure was repeated once. The cell suspension was then diluted 100-fold and plated on Heart Infusion Agar plates containing 10 µg/ml neomycin. After 40 hours of incubation at 50° C., neomycin-resistant colonies were isolated and cultured in 10 ml TSB medium, containing 10 µg/ml neomycin, for 16 hours at 30° C. Total DNA from these cultures was isolated (Holmes et al., Anal. Biochem. (1981) 114:193–197). The absence of plasmids in these cells was verified by DNA electrophoresis on agarose gels. Samples in which low molecular weight DNA was virtually absent, were rechecked for the presence of plasmid DNA by DNA transformation to B. subtilis 1-A40 (Spizizen et al., 1961). Samples lacking the ability to transform B. subtilis 1-A40 to neomycin resistance were considered plasmid minus.

To check whether integration of pElatB took place and how it took place, chromosomal DNA was isolated from the transformants (Saito-Minwa, Biochem. Biophys. Acta (1963) 72:619–632), digested with EcoRI, fractionated on 0.5% agarose gels, blotted onto nitrocellulose filters (Southern, J. Mol. Biol. (1975) 98:503–517) and hybridized with $^{32}$P-labeled nick-translated pGB33 (see EP-A-0134048). The results from this analysis are shown in FIG. 9A. The data show that illegitimate recombination of pElatB took place resulting in a strain containing a single amylase gene on a different locus of the genome as compared with the original B. licheniformis T5 amylase strain. The strain obtained containing pElatB was named TB13.

EXAMPLE 11

Construction of Strain T13F Containing Two Amylase Genes Separated by Endogenous Chromosomal Sequences In order to develop a strain containing two amylase genes separated by endogenous chromosomal DNA sequences, a fusion experiment was performed between B. licheniformis strain T5 (the original amylase gene containing amylase strain, see EP-A-013048) and strain TB13 (the randomly integrated, amylase gene containing strain). B. licheniformis strain T5 was deposited as B. licheniformis T-5a at the Centraal Bureau voor Schimmelcultures, P.O. Box 273, 3740 AG BAARN, The Netherlands on Jun. 7, 1983, under Accession Number CBS 470.83 (LMD 83.16). Protoplast fusion was performed as described in EP-A-0134048, the disclosure of which is hereby incorporated by reference. Strain TB13 was killed with iodoacetamide prior to protoplast formation. Strain T5 (neomycin sensitive) was not killed. Selection for fusants took place on the regeneration plates containing 10 µg/ml neomycin.

To check and identify potential fusants, chromosomal DNA was isolated, digested with EcoRI, fractionated on 0.5% agarose gels, blotted to nitrocellulose filters (Southern, J. Mol. Biol. (1975) 98:503–517) and hybridized with $^{32}$P-labeled nick-translated pGB33 (see EP-A-0134048). The result of this analysis is shown in FIG. 9B. One of the obtained fusants, T13F, contained two amylase genes separated by endogenous chromosomal sequences.

EXAMPLE 12

Stability of the Duplicated Amylase Genes in Strains T390 and T13F

The stability of strain T13F, a strain containing two chromosomal amylase genes separated by essential chromosomal sequences, was compared with that of strain T390, a strain with two chromosomal amylase genes located in a tandem array. Preparation of strain T390 is disclosed in European application EP-A-0134048 (page 17, Table I), where it was referred to as B. licheniformis T5 (pGB33).

Strains T13F and T390 were tested under fermentation conditions, namely 0.2 ml of an overnight TSB culture (37° C.) was inoculated in 500 ml shake flasks containing 100 ml production medium (see Example 7; after sterilization the pH was adjusted to 6.9 with NaOH) without neomycin. After incubation for 6 days at 40° C. under constant aeration, the culture was tested for neomycin-resistant colonies and amylase activity. The results of the fermentation experiments are summarized in the following Table 2.

TABLE 2

| Strain | Relative Amylase Activity | Percent of Neomycin-Resistant Cells After Fermentation* |
|---|---|---|
| T5 | 100% | — |
| TB13 | 20% | 100% |
| T13F | 120% | 100% |
| T390 | 200% | 88% |

*More than a thousand colonies were tested per strain.

To exclude the possibility of excision of one amylase gene without concomitant loss of the neomycin gene in strain T13F, 20 colonies derived from the T13F fermentation were analyzed. Chromosomal DNA from 20 randomly chosen colonies was isolated and characterized by hybridization experiments as described above. The results of 9 of these analyses are shown in FIG. 10. All strains tested contained two amylase genes, as demonstrated by the presence of two α-amylase genes-containing EcoRI fragments in their chromosomal DNA.

In contrast to the genetic stability of strain T13F, strain T390 was found to be unstable upon fermentation resulting in 12% neomycin-sensitive colonies. One of these colonies was analyzed and found to contain only one α-amylase gene (FIG. 10, Lane 4). This shows that randomly integrated amylase genes are more stable than tandemly integrated genes, under fermentation conditions.

It is evident from the above results that a prokaryotic cell may be obtained in which stable gene amplification is achieved by selecting for transformed cells in which non-tandem integration of at least two copies of the structural gene to be amplified has occurred. Integration may occur by homologous recombination or illegitimate recombination.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A stably transformed Bacillus strain host cell comprising at least two non-tandem copies of a DNA sequence encoding a polypeptide of interest, separated by intervening sequences which if deleted, the loss of said intervening sequences would be lethal to said transformed host cell, wherein said transformed host cell is produced by a method comprising the steps of:

combining a recipient Bacillus strain host cell comprising at least one copy of said DNA sequence integrated into its chromosome with either (a) a DNA construct via transformation or liposome fusion, which provides for random, non-tandem integration into said host cell chromosome, comprising at least one copy of said DNA sequence and at least one selection means from the group consisting of (i) a marker gene and (ii) a temperature-sensitive origin of replication or (b) a donor host cell comprising said DNA construct via protoplast fusion, to produce a transformed Bacillus strain host cell;

selecting for a plasmid-free transformed Bacillus strain host cell comprising at least two non-tandem copies of said DNA sequence randomly integrated into the chromosome and separated by endogenous chromosomal DNA sequences in the genome of said host cell so that deletion of said endogenous chromosomal sequences as a result of recombination between two copies of said DNA sequence is lethal to said host cell; and isolating said plasmid-free stably transformed Bacillus strain host cell.

2. The stably transformed Bacillus strain host cell according to claim 1, wherein said Bacillus strain is an alkalophilic Bacillus strain or a *B. licheniformis* strain.

3. The stably transformed Bacillus strain host cell according to claim 1, wherein said polypeptide of interest is an enzyme.

4. The stably transformed Bacillus strain host cell according to claim 1, wherein said DNA sequence is obtained from the genome of Bacillus novo species PB92.

5. The stably transformed Bacillus strain host cell according to claim 1, wherein said DNA sequence is obtained from the genome of *B. licheniformis* T5.

6. The isolated stably transformed Bacillus strain host cell according to claim 1, wherein said random non-tandem integration is by illegitimate recombination.

7. The isolated stably transformed Bacillus strain host cell according to claim 1, wherein said endogenous chromosomal DNA sequences are of less than 10 kilobase pairs.

8. The isolated stably transformed Bacillus strain host cell according to claim 1, wherein said DNA construct is linear.

9. The stably transformed Bacillus strain host cell according to claim 2, wherein said alkalophilic Bacillus strain is Bacillus novo species PB92.

10. The stably transformed Bacillus strain host cell according to claim 2, wherein said *B. licheniformis* strain is *B. licheniformis* T5.

11. The stably transformed Bacillus strain host cell according to claim 3, wherein said enzyme is a proteolytic enzyme or an amylolytic enzyme.

12. The stably transformed Bacillus strain host cell according to claim 11, wherein said proteolytic enzyme is a serine protease.

13. The stably transformed Bacillus strain host cell according to claim 11, wherein said amylolytic enzyme is α-amylase.

14. The stably transformed Bacillus strain host cell according to claim 12, wherein said serine protease comprises substantially the following amino acid sequence:

H₂N—A—Q—S—V—P—W—G—I—S—R—V—Q—A—P—A—A—H—N—R—G—L—T—G—S—G—V—K—V—A—
V—L—D—T—G—I—S—T—H—P—D—L—N—I—R—G—G—A—S—F—V—P—G—E—P—S—T—Q—D—G—N—
G—H—G—T—H—V—A—G—T—I—A—A—L—N—N—S—I—G—V—L—G—V—A—P—N—A—E—L—Y—A—V—
K—V—L—G—A—S—G—S—G—S—V—S—S—I—A—Q—G—L—E—W—A—G—N—N—G—M—H—V—A—N—L—
S—L—G—S—P—S—P—S—A—T—L—E—Q—A—V—N—S—A—T—S—R—G—V—L—V—V—A—A—S—G—N—
S—G—A—G—S—I—S—Y—P—A—R—Y—A—N—A—M—A—V—G—A—T—D—Q—N—N—N—R—A—S—F—S—
Q—Y—G—A—G—L—D—I—V—P—G—V—N—N—Q—S—T—Y—P—G—S—T—Y—A—S—L—N—G—T—S—
M—A—T—P—H—V—A—G—A—A—A—L—V—K—Q—K—N—P—S—W—S—N—V—Q—I—R—N—H—L—K—N—
T—A—T—S—L—G—S—T—N—L—Y—G—S—G—L—V—N—A—E—A—A—T—R—COOH.

15. A method for preparing a stably transformed Bacillus strain host cell comprising at least two non-tandem copies of a DNA sequence encoding a polypeptide of interest, separated by intervening sequences which if deleted, the loss of said intervening sequences would be lethal to said transformed host cell, said method comprising:

combining a recipient Bacillus strain host cell comprising at least one copy of said DNA sequence integrated into its chromosome with (a) a DNA construct via transformation or liposome fusion, which provides for random, non-tandem integration into said host cell chromosome, comprising at least one copy of said DNA sequence and at least one selection means from the group consisting of (i) a marker gene and (ii) a temperature-sensitive origin of replication or (b) a donor cell comprising said DNA construct via protoplast fusion;

selecting for a plasmid-free stably transformed Bacillus strain host cell comprising at least two non-tandem copies of said DNA sequence randomly integrated into the chromosome and separated by endogenous chromosomal DNA sequences in the genome of said host cell so that deletion of said endogenous chromosomal sequences as a result of recombination between two copies of said DNA sequence is lethal to said host cell; and isolating said plasmid-free stably transformed Bacillus strain host cell.

16. The method according to claim 15, wherein said selecting comprises:

growing said transformant comprising a DNA construct comprising a marker gene in the presence of a biocide to which said marker gene provides resistance.

17. The method according to claim 15, wherein said selecting comprises:

growing said transformant comprising a DNA construct comprising a marker gene and a temperature-sensitive origin of replication in the presence of a biocide at a non-permissive temperature.

18. The method according to claim 15, wherein said isolating comprises:

isolating chromosomal DNA from said transformants; and hybridizing said chromosomal DNA with a labeled probe comprising said DNA construct whereby said stably transformed Bacillus strain host cells are identified by detecting said label.

19. The method according to claim 15, wherein said donor cell is obtained by a method comprising:

combining a Bacillus strain cell lacking a DNA sequence encoding said polypeptide of interest with said DNA construct under fusing conditions;

isolating transformed Bacillus strain cells;

growing said transformed Bacillus strain cells at a non-permissive temperature; and identifying and isolating stably transformed Bacillus strain cells wherein said DNA construct is integrated into a location on the chromosome of said donor cell different from the location of said DNA sequence in said recipient host cell.

20. The method according to claim 15, wherein said Bacillus strain is an alkalophilic Bacillus strain or a *B. licheniformis* strain.

21. The method according to claim 15, wherein said polypeptide of interest is an enzyme.

22. The method according to claim 15, wherein said polypeptide of interest is a serine protease and has at least 70% homology with the following amino acid sequence:

```
H₂N-A-Q-S-V-P-W-G-I-S-R-V-Q-A-P-A-A-H-N-R-G-L-T-G-S-G-V-K-V-A-
V-L-D-T-G-I-S-T-H-P-D-L-N-I-R-G-G-A-S-F-V-P-G-E-P-S-T-Q-D-G-N-
G-H-G-T-H-V-A-G-T-I-A-A-L-N-N-S-I-G-V-L-G-V-A-P-N-A-E-L-Y-A-V-
K-V-L-G-A-S-G-S-G-S-V-S-S-I-A-Q-G-L-E-W-A-G-N-N-G-M-H-V-A-N-L-
S-L-G-S-P-S-P-S-A-T-L-E-Q-A-V-N-S-A-T-S-R-G-V-L-V-V-A-A-S-G-N-
S-G-A-G-S-I-S-Y-P-A-R-Y-A-N-A-M-A-V-G-A-T-D-Q-N-N-N-R-A-S-F-S-
Q-Y-G-A-G-L-D-I-V-P-G-V-N-N-Q-S-T-Y-P-G-S-T-Y-A-S-L-N-G-T-S-
M-A-T-P-H-V-A-G-A-A-A-L-V-K-Q-K-N-P-S-W-S-N-V-Q-I-R-N-H-L-K-N-
T-A-T-S-L-G-S-T-N-L-Y-G-S-G-L-V-N-A-E-A-A-T-R-COOH.
```

23. The method according to claim 15, wherein said DNA construct is pMAX-4 or pElatB.

24. The method according to claim 15, wherein said temperature sensitive origin of replication is obtained from plasmid pE194.

25. The method according to claim 20, wherein said alkalophilic Bacillus strain is a Bacillus novo species PB92 and said *B. licheniformis* strain is a *B. licheniformis* strain T5.

26. The method according to claim 21, wherein said enzyme is a serine protease or an amylase.

27. The method according to claim 26, wherein said serine protease has substantially the following amino acid sequence:

```
H₂N-A-Q-S-V-P-W-G-I-S-R-V-Q-A-P-A-A-H-N-R-G-L-T-G-S-G-V-K-V-A-
V-L-D-T-G-I-S-T-H-P-D-L-N-I-R-G-G-A-S-F-V-P-G-E-P-S-T-Q-D-G-N-
G-H-G-T-H-V-A-G-T-I-A-A-L-N-N-S-I-G-V-L-G-V-A-P-N-A-E-L-Y-A-V-
K-V-L-G-A-S-G-S-G-S-V-S-S-I-A-Q-G-L-E-W-A-G-N-N-G-M-H-V-A-N-L-
S-L-G-S-P-S-P-S-A-T-L-E-Q-A-V-N-S-A-T-S-R-G-V-L-V-V-A-A-S-G-N-
S-G-A-G-S-I-S-Y-P-A-R-Y-A-N-A-M-A-V-G-A-T-D-Q-N-N-N-R-A-S-F-S-
Q-Y-G-A-G-L-D-I-V-P-G-V-N-N-Q-S-T-Y-P-G-S-T-Y-A-S-L-N-G-T-S-
M-A-T-P-H-V-A-G-A-A-A-L-V-K-Q-K-N-P-S-W-S-N-V-Q-I-R-N-H-L-K-N-
T-A-T-S-L-G-S-T-N-L-Y-G-S-G-L-V-N-A-E-A-A-T-R-COOH.
```

28. An isolated stably transformed Bacillus strain host cell comprising at least two non-tandem copies of a DNA sequence encoding a polypeptide of interest randomly integrated into the chromosome and separated by endogenous chromosomal sequences in the genome of said host cell, wherein said non-tandem copies of said DNA sequence and said endogenous chromosomal sequences permit selection for said stably transformed Bacillus strain host cell and wherein deletion of said endogenous chromosomal sequences in the genome of said host cell as a result of recombination between two copies of said DNA sequence is lethal to said host cell.

29. Bacillus PBT108, PBT122, or T13F.

* * * * *

UNITED STATES PATENT AND TRADEMARK OFFICE
CERTIFICATE OF CORRECTION

PATENT NO. : 5,733,723
DATED : March 31, 1998
INVENTOR(S) : van Eekelen et al.

Figure 5A:
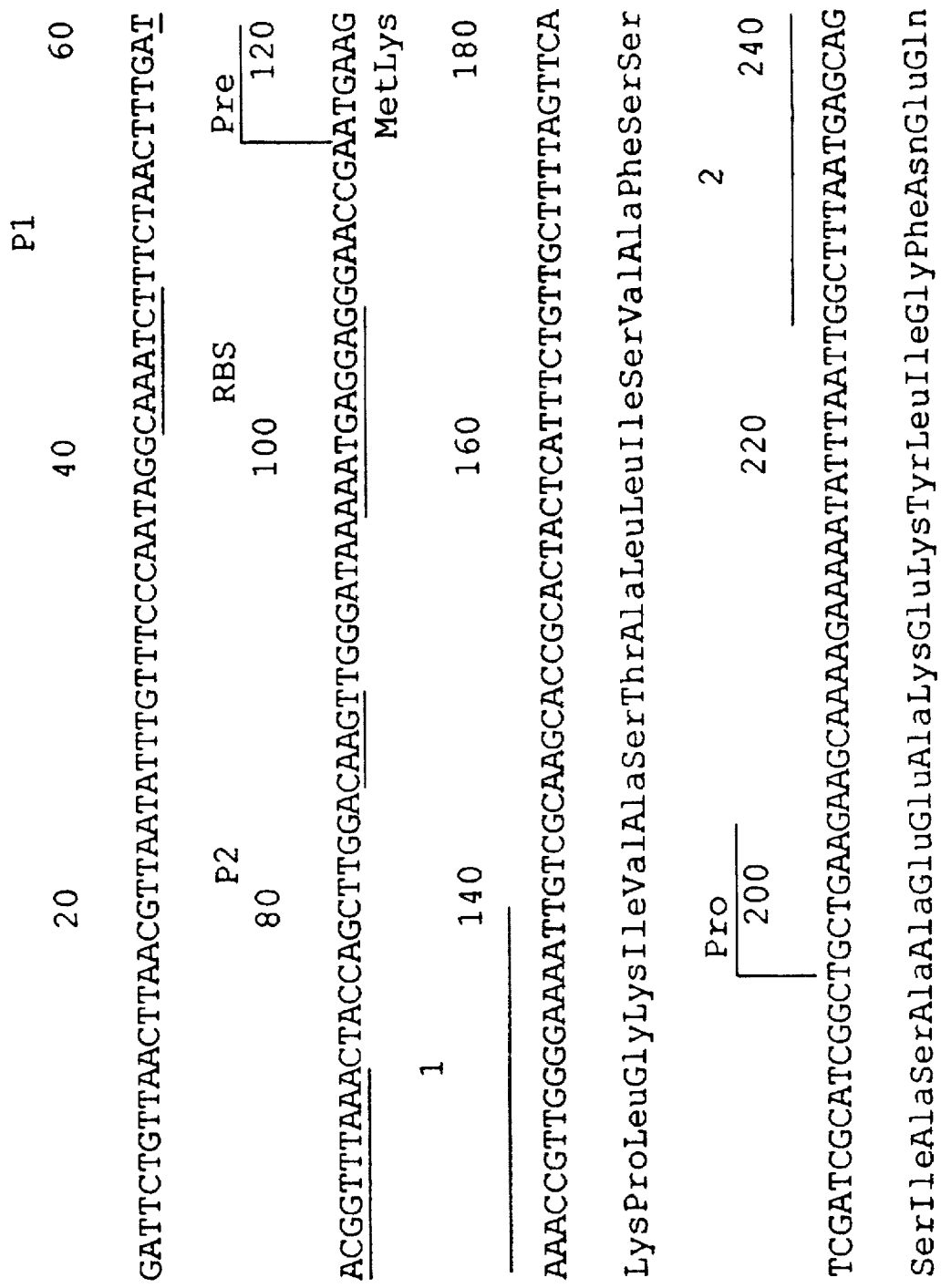

It is certified that error appears in the above-identified patent and that said Letters Patent is hereby corrected as shown below:

Column 4,
Line 50, change "FIG. 5" to -- FIG. 5A-F --

Column 8,
Line 10, change "vital" to -- viral --

Column 11,
Line 16, change "deposited" to -- (deposited --
Line 20, change "Microbiologic" to -- Microbiologie --

Column 12,
Line 3, change "fop" to -- for --
Line 18, change "pUBS10" to -- pUBS100 --

Column 13,
Line 53, change "Tryprone" to -- Tryptone --
Line 58, change "dilated" to -- diluted --
Line 62, change "aid" to -- and --

Column 14,
Line 12, change "nitrecellulose" to -- nitrocellulose --

Columns 17-18,
Line 62, change
"Q-Y-G-A-G-L-D-I-V-P-G-V-N-N-Q-S-T-Y-P-G-S-T-Y-A-S-L-N-G-T-S-" to
-- Q-Y-G-A-G-L-D-I-V-A-P-G-V-N-V-Q-S-T-Y-P-G-S-T-Y-A-S-L-N-G-T-S- --

Columns 19-20,
Line 26, change
"Q-Y-G-A-G-L-D-I-V-P-G-V-N-N-Q-S-T-Y-P-G-S-T-Y-A-S-L-N-G-T-S-" to
-- Q-Y-G-A-G-L-D-I-V-A-P-G-V-N-V-Q-S-T-Y-P-G-S-T-Y-A-S-L-N-G-T-S- --

UNITED STATES PATENT AND TRADEMARK OFFICE
CERTIFICATE OF CORRECTION

PATENT NO. : 5,733,723
DATED : March 31, 1998
INVENTOR(S) : van Eekelen et al.

It is certified that error appears in the above-identified patent and that said Letters Patent is hereby corrected as shown below:

Columns 19-20,
Line 50, change
"Q–Y–G–A–G–L–D–I–V–P–G–V–N–N–Q–S–T–Y–P–G–S–T–Y–A–S–L–N–G–T–S–" to
-- Q–Y–G–A–G–L–D–I–V–A–P–G–V–N–V–Q–S–T–Y–P–G–S–T–Y–A–S–L–N–G–T–S– --

Signed and Sealed this

Seventh Day of May, 2002

Attest:

JAMES E. ROGAN
Attesting Officer  Director of the United States Patent and Trademark Office